United States Patent [19]

Caruthers et al.

[11] Patent Number: 4,500,707

[45] Date of Patent: Feb. 19, 1985

[54] NUCLEOSIDES USEFUL IN THE PREPARATION OF POLYNUCLEOTIDES

[75] Inventors: Marvin H. Caruthers, Boulder, Colo.; Mark D. Matteucci, San Francisco, Calif.

[73] Assignee: University Patents, Inc., Westport, Conn.

[21] Appl. No.: 358,877

[22] Filed: Mar. 16, 1982

Related U.S. Application Data

[63] Continuation-in-part of Ser. No. 247,144, Mar. 24, 1981, Pat. No. 4,458,066, which is a continuation-in-part of Ser. No. 126,025, Feb. 29, 1980, abandoned.

[51] Int. Cl.³ .................. C07H 19/06; C07H 19/10; C07H 19/16; C07H 19/20
[52] U.S. Cl. ........................ 536/27; 536/28; 536/29
[58] Field of Search .................. 536/27, 28, 29; 424/180, 176, 361

[56] References Cited

U.S. PATENT DOCUMENTS 4,373,071 2/1983 Itakura .................. 536/28

OTHER PUBLICATIONS

Chemical Abstracts, vol. 95, p. 744, col. 2, Abst. No. 25493n, 1981.
Hackh's Chemical Dictionary, edited by Julius Grant, McGraw-Hill Book Co., New York, 1972, p. 37.
Organic Chemistry, Allyn and Bacon, Inc., Boston, 1966, pp. 718-719.

*Primary Examiner*—Blondel Hazel
*Attorney, Agent, or Firm*—George M. Yahwak

[57] ABSTRACT

New and useful intermediate nucleotides bound to an inorganic polymer support, including the preparation thereof, and processes for the conversion to oligonucleotides which are especially useful for the synthesis of polynucleotides, particularly ribonucleic (RNA) and deoxyribonucleic acids (DNA).

16 Claims, 1 Drawing Figure

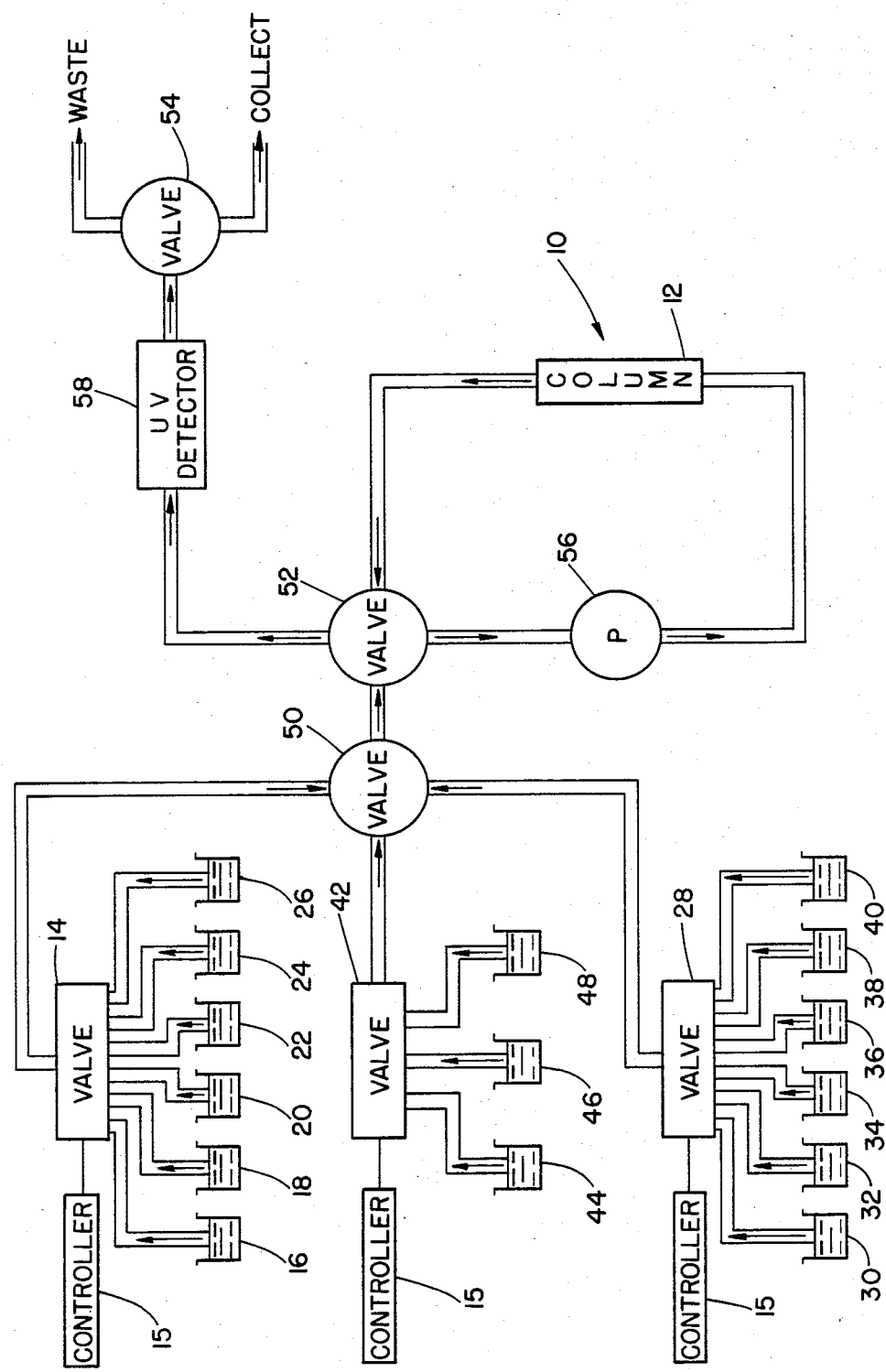

NUCLEOSIDES USEFUL IN THE PREPARATION OF POLYNUCLEOTIDES

The inventions described herein were made in the course of work under a grant or award from the Department of Health, Education and Welfare.

This application is a continuation-in-part of copending application Ser. No. 247,144, filed Mar. 24, 1981 now U.S. Pat. No. 4,458,066, which is a continuation-in-part of copending application Ser. No. 126,025 filed Feb. 29, 1980, now abandoned.

BACKGROUND OF THE INVENTION

1. Field of the Invention

The present invention relates to modified inorganic polymers and to methods of making such modified inorganic polymers. Additionally, it relates to methods of producing polynucleotides utilizing said modified inorganic polymers as a support structure.

2. Prior Art

Numerous attempts have been made to develop a successful methodology for synthesizing sequence defined oligonucleotides. However, the stepwise synthesis of polynucleotides, and specifically oligonucleotides still remains a difficult and time consuming task, often with low yields. One prior art technique has included the use of organic polymers as supports during polynucleotide synthesis. Classically the major problems with polymer supported synthesis strategies has been inherent in the nature of the polymer support. Various prior art polymers used in such syntheses have proven inadequate for reasons such as: (1) slow diffusion rates of activated nucleotides into the support; (2) excessive swelling of various macroporous, low crosslinked support polymers; and (3) irreversible absorption of reagents onto the polymer. See for example, V. Amarnath and A. D. Broom, *Chemical Reviews* 77, 183–217 (1977).

Modified inorganic polymers are known in the prior art, primarily for use as absorption materials, for example, in liquid chromatography. The attachment of nucleosidephosphates to silica gel using a trityl linking group is described in the prior art (H. Koster, *Tetrahedron Letters*, 1527–1530, 1972) but the method is apparently applicable only to pyrimidine nucleosides. The cleavage of the nucleoside from the silica support can only be accomplished with acid to which the purine nucleosides are sensitive.

The production of phosphotriester derivatives of oligothymidylates is described in the literature (R. L. Letsinger and W. B. Lunsford, *Journal of the American Chemical Society*, 98:12, 3655–3661) by reaction of a phosphorodichloridite with a 5'-O blocked thymidine and subsequent reaction of the product with a 3'-O—blocked thymidine followed by oxidation of the resulting phosphite to a phosphate and removal of blocking groups to obtain the phosphotriesters; using this procedure, the tetramer and pentamer products, dTpTpTpT and dTpTpTpTpT in which T is thymidine were prepared. Unfortunately, the process requires separation and purification of products at each stage to ensure proper sequencing of the added nucleosides. Separation techniques including precipitation and washing of precipitates are necessary to implement each successive stage reaction.

BRIEF DESCRIPTION OF THE INVENTION

The present invention provides new and useful modified inorganic polymers. It also provides a new process for producing such inorganic polymers. In general, the modified inorganic polymer supports of the present invention comprise the inorganic polymer to which is chemically bound a nucleoside. The chemical bonding of the nucleoside moiety to the polymer is by means of reactive groups on the polymer which react with reactive groups of the nucleoside molecule. Representative combinations of such groups are amino with carboxy to form amide linkages between the nucleoside and the support, or hydroxy with carboxy to form ester linkages between the respective moieties.

To accomplish the requisite chemical bonding, each of the reactants must of course contain the necessary reactive groups. Thus, the polymer support can be provided with terminal carboxy functionality which will react with hydroxyl and/or amino groups of the nucleoside. Alternatively, the nucleoside can be provided with carboxy functionality by acylation of the hydroxyl and/or amino groups using a dicarboxylic acid and the carboxy-functional nucleoside reacted with hydroxy or amino groups of the polymer support. Hydroxy and amino functionality where not present on the inorganic support can be introduced by known methods. For example, with silica supports, amino functionality can be introduced by reaction with aminoalkylsilyl halides.

Of course, the nucleoside moiety of the present modified inorganic polymers can include more than one nucleoside and may include a number of nucleosides condensed as oligonucleotides with the oligonucleotide being attached to the inorganic polymer support through the single chemical linkage, e.g. ester linkage.

The thus modified inorganic polymer supports are useful in the stepwise addition of nucleosides or oligonucleotides to the original nucleoside moiety of the support by a series of process steps as described hereinafter. Subsequently, the polynucleotides so produced are released from the polymer support and recovered from the polymer by a series of process steps including alkali hydrolysis of the chemical bond between the polynucleotide and the support.

The present invention is particularly useful in the chemical synthesis of any deoxyribonucleic acids (DNA) and ribonucleic acids (RNA) which contain any deoxynucleotides, nucleotide, polynucleotide, and polydeoxynucleotide, as well as polypeptides. Thus natural DNA and RNA as well as new DNA and RNA can be synthesized.

A wide variety of inorganic polymers can be employed in the present invention and these include, for example, silica, porous glass, aluminosilicates, borosilicates, metal oxides such as alumina and nickel oxide, and various clays. The polymer should be substantially insoluble in the reaction solvents employed and relatively chemically inert to the reagents employed during processing, except of course for the chemical reactivity required to form the hereinbefore-described chemical bond with the initial nucleoside through which the eventual polynucleoside is attached to the support.

The process of the present invention is accomplished by treatment of the nucleotide or nucleoside-modified inorganic polymer support by a series of sequential steps whereby each series results in the addition of nucleotide to the modified support until the desired sequence of nucleotides is obtained. The series of sequential steps is as follows:

(a) coupling of a selected nucleoside through a phosphite linkage to the nucleoside bound to the polymer support, i.e. the nucleoside-modified support;

(b) optionally, but preferably blocking unreacted hydroxyl groups on the nucleotide of the polymer support;

(c) oxidation of the phosphite linkage of step (a) to form a phosphate linkage.

(d) removal of protecting group from the selected nucleoside described in step (a) to regenerate a reactive site for the next cycle of these steps.

Each nucleoside is added sequentially to the polymer support by repetition of steps a, b, c and d until the final oligonucleotide is obtained, after which the oligonucleotide is then removed from the support by hydrolysis reaction which can also remove blocking groups from the oligonucleotide molecule. The removal of blocking groups and hydrolytic cleavage of the oligonucleotide from the support can be accomplished stepwise, which is preferred, or in a single hydrolysis reaction.

The nucleoside-modified support is prepared by covalently coupling a nucleoside to the inorganic polymer using a suitable coupling agent through the 3'- or the 5'-OH of the starting nucleoside. This is accomplished with the starting nucleoside being blocked in either the 3'- or the 5'-OH, and the nucleoside is coupled through the unblocked hydroxy group to the polymer support by the coupling agent. After condensation, residual reactive groups, e.g. carboxy groups, which did not react can be blocked by suitable means, e.g. conversion of carboxy groups to carboxamide by reaction with simple amines. Thereafter, the blocked 3'- or 5'-hydroxy group is converted to free hydroxy by removal of the blocking group and the free hydroxy group is available for condensation with a selected nucleoside containing a phosphite linking groups as in step (a) hereinbefore described.

A variety of coupling agents or groups on the polymer support can be used to covalently link the initial nucleoside or oligonucleotide to the polymer support. Representative groups include amino, especially primary amino, hydroxy, thiol, sulfonic acid, phosphorous and phosphoric acid, particularly in the form of acid halides, especially chloro and bromo and carboxy, among others. These reactive groups are conveniently attached to the polymer support commonly through a hydrocarbyl radical such as an alkylene or phenylene divalent radical, one valence position being occupied by the chain bonding and the remaining attached to the reactive groups. Such hydrocarbyl groups may contain up to about 10 carbon atoms, preferably up to about 6 carbon atoms. Alkylene radicals are usually preferred containing 2–4 carbon atoms in the principal chain.

The nature of the reactive group which bonds the nucleoside to the polymer support is not critical but should preferably be readily hydrolyzable to permit separation of the oligonucleotide product from the polymer support at the conclusion of the preparative process.

If desired, the aforesaid coupling groups can be present on the nucleoside for reaction with reactive groups, e.g. hydroxy or amino, on the support polymer. Normally it is preferred to have the coupling groups on the polymer support.

The process of this invention, and the new and useful nucleoside-modified inorganic polymer support used therein are particularly advantageous in that they provide a rapid synthetic route to oligonucleotides and oligodeoxy-nucleotides which is characterized by high yields and high purity. Each mononucleotide addition is usually complete in as little as 0.5 minutes, particularly where excess phosphite is used. Generally, the reaction is allowed to digest for a longer period, e.g. from as little as five minutes up to several hours.

While the invention can be implemented with a variety of inorganic polymers, it will be described herein in more detail utilizing silica gel as the polymer support. A particularly preferred silica gel is macroporous silica which is used in high performance liquid chromatography (hplc). In addition, the invention will be described using deoxynucleotides but it should be understood that ribonucleotides can be substituted therefor to obtain similar results.

As employed herein, the terms nucleoside, nucleotide and oligonucleotide are intended to include the deoxy counterparts which differ only in the absence of a hydroxy group in the 2' position. Thus, these terms include structures wherein the 2' position substituent is H or OH (as shown hereinafter by substituent A in formulae I, II and III).

DESCRIPTION OF THE PREFERRED EMBODIMENTS

(A) Preparation of nucleoside-modified support

The silica gel support is preferably linked to the silica gel support through a linkage which is readily hydrolyzable, preferably with a weak base such as ammonium hydroxide. The most preferred linkage is an ester linkage which readily hydrolyzes in a weak base such as ammonium hydroxide. This linkage can be accomplished by first linking carboxy functionality to the support or by preforming the ester linkage on the nucleoside by esterification followed by condensation of the esterified nucleoside through the esterifying acid moiety to the support.

The first of these embodiments can be accomplished by the following steps:

(1) conversion of silica gel to a matrix containing aminoalkyl groups or hydroxyalkyl groups covalently bound thereto;

(2) reaction of the aminoalkyl silica with a dicarboxylic acid to form an amide or ester linkage and carboxy functionality;

(3) blocking unreacted silanol OH groups;

(4) condensation of the free carboxy groups of the silica with the free hydroxy (3'- or 5'-) of the selected nucleoside; and (5) blocking unreacted carboxy groups by conversion to unreactive derivatives, e.g. amides.

The alternative embodiment involves the following steps:

(1) conversion of silica gel to matrix containing aminoalkyl groups or hydroxyalkyl groups;

(2) block unreacted silanol OH groups;

(3) join the derivatized silica gel through amide or ester formation to the free carboxy group of a selected nucleoside which has been modified to contain the half ester of a dicarboxylic acid; and (4) blocking unreactive amino or hydroxy groups on the silica gel support, e.g. using acetic anhydride. Both embodiments give the same product from identical reactants. The second embodiment however is preferred since it leads to more control of the amount of nucleoside loaded onto the silica gel. Additionally, the second embodiment leads to more nucleoside joined to the silica gel (approximately 100–120 μmole/g compared to 10–40 μmole/g by the first embodiment).

Preferably, the nucleoside is linked to the silica gel through the 3'-OH group rather than the 5'-OH leaving the 5'-OH available for linkage through phosphite to the added nucleoside. Thus, linkage of the added nucleoside occurs at the 3'-OH group and the 5'-OH remains available for linkage to a further added nucleoside.

Accordingly, to accomplish the desired linkages at the 3'-OH and 5'-OH respectively, the initial nucleoside is linked through the 3'-OH to the silica gel by the coupling reaction previously defined herein. This is accomplished by blocking the 5'-OH e.g. by use of trityl groups, such as the dimethoxytrityl group, which are preferred since they are readily removed after the initial 3'-OH coupling reaction occurs.

When the initial nucleoside includes amino groups, e.g. guanosine, adenosine, cytidine, deoxyguanosine, deoxyadenosine and deoxycytidine, it is preferred to block these groups using known acylating techniques, e.g. with acetic acid, benzoic acid, isobutyric acid and like acids and such blocking group can be removed when convenient, usually after the final oligonucleotide is obtained.

The aminoalkyl groups are incorporated on the silica gel by reaction of aminoalkyl-trialkoxysilane which is conveniently accomplished by refluxing in a solvent, e.g. toluene, for several hours. Suitable reagents include aminopropyltriethoxysilane, 4-aminobutyltrimethoxysilane, 4-aminobutyltriethoxysilane, 2-aminoethyltriethoxysilane and others.

The dicarboxylic acid employed in forming the ester linkage of deoxynucleoside to the silica gel can be any of a variety such as succinic, glutaric, adipic, phthalic, maleic and similar such dicarboxylic acids of the aliphatic or aromatic type containing preferably up to about 10 carbon atoms. Esterification with the dicarboxylic acid is best accomplished by using the acid anhydride to assure monoesterification.

The product produced, i.e. the nucleoside-modified silica gel, can be represented by the following formula:

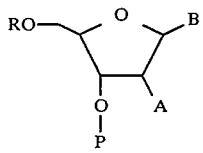

wherein B is the nucleoside or deoxynucleoside base; Ⓟ represents the silica support and the covalent linking group which is preferably represented by the formula (silica gel)(CH$_2$)$_n$NHCOZCO— in which n is an integer from 1–5 and Z is divalent hydrocarbyl radical including alkyl, alkenyl, cycloalkyl, aryl and aralkyl of up to about 10 carbon atoms; A is H or OR; and R is H or a blocking group, e.g. trityl, methoxytrityl, dimethoxytrityl, dialkylphosphite, pivalylisobutyloxycarbonyl, t-butyldimethylsilyl, and similar such blocking groups.

Formation of phosphitic-linked oligonucleosides

The deoxynucleoside-modified silica gel is condensed with a selected nucleoside through formation of a triester phosphite linkage between the 5'-OH of the deoxynucleoside of the silica gel and the 3'-OH of the selected deoxynucleoside. The phosphite linkage can be produced by first incorporating the phosphite group onto the 5'-OH of the nucleoside on the silica gel followed by condensation with the added nucleoside through the 3'-OH. Alternatively, and preferably, the phosphite group is incorporated into the added nucleoside at the 3'-OH (the 5'-OH being blocked as by tritylating) and the resulting nucleoside phosphite then reacted with the 5'-OH of the nucleoside on the silica gel.

The deoxynucleoside-modified silica gel can also be condensed with a selected nucleoside through formation of a triester phosphite linkage between the 3'-OH of the deoxynucleoside of the silica gel and the 5'-OH of the selected deoxynucleoside. The phosphite linkage can be produced by first incorporating the phosphite group onto the 3'-OH of the nucleoside on the silica gel followed by condensation with the added nucleoside through the 5'-OH. Alternatively and preferably by this approach, the phosphite group is incorporated into the added nucleoside at the 5'-OH (the 3'-OH being blocked as by tritylating using art form procedures) and the resulting nucleoside phosphite then reacted with the 3'-OH of the nucleoside on the silica gel.

The general reaction can be represented by the following:

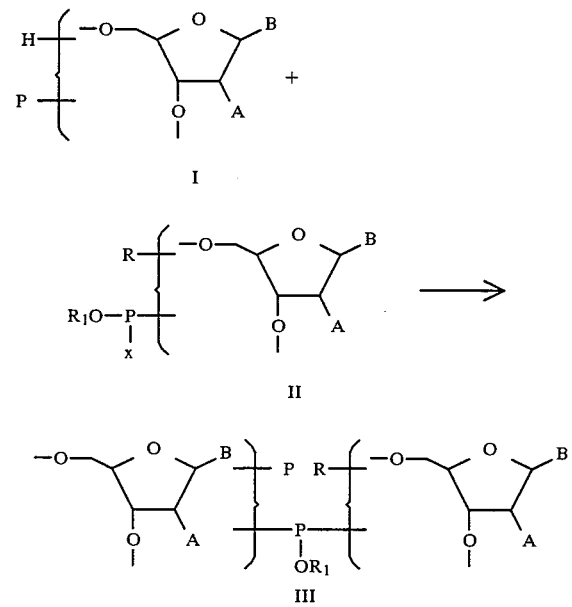

The preferred reaction is represented as follows:

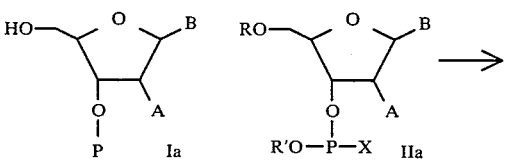

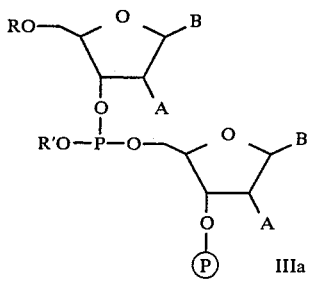

wherein A, B and Ⓟ are as previously defined, R is a blocking group as previously defined, R' is lower alkyl and X is halogen, preferably Cl or Br, or a secondary amino group attached through the amino nitrogen. The secondary amino group represented by substituent X is preferably one which is formed by removal of the hydrogen atom from a ring nitrogen of a nitrogen heterocyclic compound which contains unsaturated bonds in the ring structure. Exemplary nitrogen-containing heterocyclics include tetrazole, substituted imidazoles such as nitroimidazole, indole pyrazole, imidazole, benzimidazole, isoindole, pyrrole, triazole, dioxazole and similar heterocyclics, as well as analogs and homologs thereof.

When X is such a secondary group, the resulting product is very reactive and somewhat unstable at ordinary temperatures. In present experience, these compounds should be freshly prepared as needed, or alternatively they can be prepared, isolated and stored in sealed containers at reduced temperature, usually well below 0° C. and usually at about −20° C.

The removal of the blocking group R permits reaction with a further nucleoside of formula II and repeat reaction gives rise to the polynucleotide of determined sequence of nucleotides attached to the silica gel through the covalently-bonded linking group, e.g. ester linking group.

The phosphite linking group is introduced into the nucleoside moiety of the silica gel at the 5'-OH position or the 3'-OH position of the added nucleoside by reaction with a hydrocarbyl (as previously defined herein) phosphorodichloridite, e.g. methyl phosphorodichloridite, preferably in the presence of a base, such as an organic amine. The resulting compound of formula II can be stored in solvent for about one week under an inert gas such as nitrogen or argon and temperatures below about −20° C.

The reaction of compounds of formula I with those of formula II is effected in the presence of a base, such as an organic amine, preferably tertiary organic amines, e.g. pyridine, lutidines and similar amines.

Blocking Reactions

After condensation of the selected nucleoside through phosphite linkage to the nuceloside or oligonucleotide attached to the silica gel support, a small but significant amount (about 1–5%) of the nucleoside or oligonucleotide attached to the silica gel does not react with the added nucleoside. These unreactive moieties preferably are capped or blocked in order to prevent the formation of several deoxyoligonucleotides with heterogeneous sequences. This capping or blocking step can be accomplished by reaction with a very reactive phosphite to form a 5'-phosphite ester group, a relatively nonhydrophobic triester. For example, diethoxytriazolylphosphine can be used to form the diethyl phosphite-5'-deoxynucleoside triester. Corresponding di-lower alkoxy nitrogen-containing heterocyclylphosphines can be used in lieu of the triazolylphosphine, e.g. tetrazolyl, imidazolyl and 4-nitroimidazolyl phosphine, to produce the corresponding di-lower alkyl triester. These nitrogen-heterocyclylphosphines are prepared from the corresponding phosphinyl chloride; of course, the phosphinyl chloride can be used to phosphinylate the nucleoside but the nitrogen heterocyclyl phosphines are preferred since their use leads to higher yields of oligonucleotide.

More traditional blocking or capping groups can be employed such as acid anhydrides like acetic anhydride and arylisocyanates like phenyl isocyanate but these react more slowly with the unblocked 5'-hydroxy group. When acetylation with acid anhydrides, e.g. acetic anhydride, is conducted in the presence of tertiary amines, especially di-loweralkylaminopyridines like dimethylaminopyridine, acylation occurs rapidly and this procedure is preferred for blocking especially the 5'-hydroxy group. The dialkylphosphite capping group can also be used. The resulting triester is relatively nonhydrophobic and a preferred purification involves reverse phase high performance liquid chromatography which assures separation of the nonhydrophobic by-product from the product containing the hydrophobic 5'-O-dimethoxytrityl group.

To block unreacted silanol hydroxy groups on the silica gel before nucleoside addition, the use of trialkoxysilyl chloride is preferred, although blocking can also be accomplished by acylation with hydrocarbylmonocarboxylic acids, preferably containing up to 10 carbon atoms, such as acetic, benzoic, butyric, isobutyric and naphthoic acids.

Oxidation of phosphite to phosphate

The oxidation is normally carried out using iodine as oxidizing agent using standard procedures. Alternatively, the oxidation can also be accomplished by reaction with peroxides like tertiary butyl peroxide and benzoyl peroxide as well as hydroperoxides. The use of hydrogen peroxide can lead to the formation of side products and is not preferred.

Oxidation should be effected before further condensation of nucleoside is attempted to obtain best yields. Attempts to defer oxidation until after all condensation reactions are completed have resulted in reduced yield of oligonucleotides due to formation of side products.

The removal of blocking groups is accomplished by art recognized procedures using mild bases such as ammonium hydroxide whether at room temperature or at elevated temperature.

In stepwise removal of blocking groups, it is preferred to first remove the alkyl group, e.g. methyl, from the phosphotriesters using triethylammonium thiophenoxide in solvent, e.g. dioxane or tetrahydrofuran. Thereafter, the product is treated with ammonium hydroxide at room temperature (20° C.) to hydrolyze the ester linkage joining the oligonucleotide to the support. Then N-acyl blocking groups, e.g. acetyl, benzoyl, and isobutyryl, are removed by warming at 50° C. for about 12 hours.

The removal of trityl blocking groups is conveniently effected employing Lewis acids, particularly zinc bromide, although other Lewis acids have also been effective, e.g. $AlCl_3$, $BF_3$ and $TiCl_4$. Usually nitromethane is used as solvent for this reaction although other solvents such as tetrahydrofuran can be used, as well as mixed solvents such as nitromethane and a lower alkanol, such as methanol. Alternatively, protic acids such as toluenesulfonic acid can be used to remove the blocking group. With purine nucleoside-containing products, however, some depurination can occur when protic acids are employed and therefore the use of Lewis acids is preferred for removal of the blocking group from purine containing products.

The products as obtained after hydrolysis can be purified by standard procedures after separation from the inorganic polymer support. Two purification schemes are particularly useful. One scheme involves purification by reverse phase hplc of trityl containing oligonucleotides *after* of the methyl group from phosphotriesters and *after* removal of N-acyl blocking groups. Material purified via hplc is then treated with acetic acid to remove the trityl ether. The alternative scheme is as follows. An oligonucleotide free of methyl phosphate protecting groups and N-acyl blocking groups is next treated with acetic acid. The oligonucleotide reaction mixture completely free of protecting groups is then purified by electrophoresis on polyacrylamide. Irradiation of the gel with ultraviolet light visualizes the product. The product band imbedded in the gel is removed (by cutting the gel with a razor blade) and the oligonucleotide freed of the gel by known art procedures.

Employing the hereindescribed process, oligonucleotides containing up to 10-30 nucleoside units can be produced. The oligonucleotides can be converted by $T_4$-ligase and $T_4$-kinase to form a DNA sequence of choice by known enzymological reactions.

DESCRIPTION OF THE DRAWING

The accompanying drawing is a schematic flow diagram of the apparatus of the present invention.

More specifically, and with reference now to the drawing, an apparatus is illustrated to accomplish the foregoing. The column 10 is packed appropriately with solid silica gel matrix 12, derivatized as described herein.

Valve 14 is appropriately programmed under control of valve controller 15 to select among the four active reagents contained in reservoirs 16, 18, 20, and 22, and the wash solvents contained in reservoirs 24 and 26. Valve 14 will permit the independent selection from any reservoir in any order without the need to sequence through intervening reservoirs. Thus, for example, the reagent from reservoir 16 may be selected, and immediately thereafter the wash solvent from reservoir 24. These reagents are required for chain elongation in accordance with the teaching of the method of this invention and are maintained at room temperature for use therein.

Valve 28, is appropriately programmed under control of controller 15' to select among the five nucleoside-active phosphite triester contained in reservoirs 30, 32 34, 36 and 38, and the wash solvent in reservoir 40. Once again, valve 28 permits independent selection (to prevent cross contamination) as described above. In addition, the reservoirs 30-38 are designed to maintain the adducts at room temperature and the valve 28 to allow for the passage therethrough at this temperature.

Valve 42 is under the contro of programmed controller 15" for the selection of cleavage reagents contained in reservoirs 44 and 46 and a wash solvent in reservoir 48. These reagents and solvent are necessary to cleave the oligonucleotide from the support matrix 12 in column 10 and are maintained at room temperature.

The valve 50 operates in conjunction with pump 56 to selectively convey solvents, reagents or adducts from the valve 14, 28 and 42 towards the valve 52. In turn, this valve 52, under suitable control of a valve controller (not illustrated) selects between flow through the column 10 and uv detector 58 or recycling through column 10. Valve 54 is controlled to direct the flow from uv detector either to waste or collection. The uv detector 58 is utilized in the control of the system, through suitable feedback control means (not illustrated).

The programmed operation of the system is illustrated schematically in Table I below. This program illustrates the protocol for the addition of one nucleoside and then cleavage of the chain from support 12. It will be apparent that the system may be expanded and/or modified to accomodate the addition of more than one nucleotide, and that the entire system will preferably operate under control of a suitably programmed microprocessor computer.

The apparatus has particular applicability for automated operation, details of which are within the preview of one skilled in the art.

TABLE I

| Step | Duration | Valve 14, 28, 42/ Selection Anode | Valve 50 Selection Anode | Valve 52 Selection Anode | Valve 54 Selection Anode | Pump Speed |
| --- | --- | --- | --- | --- | --- | --- |
| 1 | 2 min. | V-14/16 | V-14 | Flush | Waste | L |
| 2 | 60 min. | V-14/16 | V-14 | Recycle | " | L |
| 3 | 5 min. | V-14/24 | V-14 | F | " | H |
| 4 | 5 min. | V-14/26 | V-14 | F | " | H |
| 5 | 2 min. | V-14/18 | V-14 | F | " | L |
| 6 | 2 min. | V-14/18 | V-14 | R | " | L |
| 7 | 5 min. | V-14/26 | V-14 | F | " | H |
| 8 | 2 min. | V-14/20 | V-14 | F | " | L |
| 9 | 2 min. | V-14/20 | V-14 | R | " | L |
| 10 | 2 min. | V-14/24 | V-14 | F | " | H |
| 11 | 3 min. | V-28/40 | V-28 | F | " | H |
| 12 | 20 sec. | V-28/30 | V-28 | F | " | L |
| 13 | 5 sec. | V-28/30 | V-28 | F | " | L |
| 14 | 60 min. | V-28/30 | V-28 | F | " | L |
| 15 | 10 sec. | V-28/30 | V-28 | R | " | L |
| 16 | 30 sec. | V-28/30 | V-28 | F | Collect | L |
| 17 | Stop | | | | | |
| 18 | 2 min. | V-14/22 | V-14 | F | Waste | L |
| 19 | 30 min. | V-14/22 | V-14 | R | " | L |
| 20 | 5 min. | V-14/26 | V-14 | F | " | H |
| 21 | 5 min. | V-14/24 | V-14 | F | " | H |

TABLE I-continued

| Step | Duration | Valve 14, 28, 42/ Selection Anode | Valve 50 Selection Anode | Valve 52 Selection Anode | Valve 54 Selection Anode | Pump Speed |
|---|---|---|---|---|---|---|
| | | One Nucleotide Added; Cleavage Sequence: | | | | |
| 1 | 2 min. | V-42/44 | V-42 | F | Waste | L |
| 2 | 60 min. | V-42/44 | V-42 | R | " | L |
| 3 | 5 min. | V-42/48 | V-42 | F | " | H |
| 4 | 30 sec. | V-42/46 | V-42 | F | " | H |
| 5 | 180 min. | V-42/46 | V-42 | R | " | L |
| 6 | 10 min. | V-42/46 | V-42 | F | Collect | L |
| 7 | 10 min. | V-42/48 | V-42 | F | " | L |

The silica gel which is used as starting material in the production of the modified silica gels of the present invention is not critical. Silica gel particles in the range of from about 5 μm to about 1000 μm are useful, with particles in the range of about 10 μm to about 50 μm being preferred. In a similar manner pore size is not critical. Pore sizes in the range of about 50 Å to about 2000 Å are preferred.

The modified silica gels of the present invention: (1) allow relatively rapid diffusion of activated nucleotides, and other reagents into the support; (2) avoid swelling; and (3) resist adsorption of reagents. Additionally, the modified silica gels of the present invention are (1) insoluble in most solvents; (2) in use as support matrices, allow solvents and unwanted reaction products to be easily washed from the matrix, while maintaining the desired reaction products in place and capable of continuous processing; and (3) allow the supported material to react relatively rapidly and in high yield, for example, in cylindrical condensation.

The modified silica gel employed to react with the initial nucleoside of the oligonucleotide chain to form the initial reactive material is prepared by art-recognized procedures. The production of a variety of functional groups on the surface of the silica gel suitable for reaction with the hydroxy (3'- or 5'-) of the initial nucleoside can be effected using known methods, e.g. methods described in U.S. Pat. Nos. 3,519,538; 3,419,517; 3,652,761; and 3,669,841.

The preferred method for the present invention is to introduce amino funtionality on the silica by reaction with an aminoalkyl silane derivative, e.g. by reaction of a trialkoxy 3-aminopropylsilane such as triethoxy 3-amino-propylsilane with the silica support to form the covalent linkage:

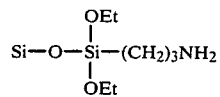

and the amino group is reacted with one carboxy group of a dicarboxylic acid therefor giving rise to carboxy functionality on the silica gel where condensation of amino and carboxy occur. The silica gel can next be treated to block unreacted silanol groups with suitable blocking agents, e.g. trialkylhalosilanes such as trimethylchlorosilane or the bromo analog.

The resulting carboxy-derivatized silica can then be reacted with the hydroxy group (3'- or 5'-) of the first added nucleoside.

Alternatively, as previously indicated herein, the dicarboxylic acid can be reacted with the selected nucleoside to form a monoester at the 3'-O or 5'-O and the resulting ester containing a free carboxy group in the esterifying radical can be condensed with the amino-derivatized silica to form the same covalent linkage between nucleoside and silica support. Any unreacted amino groups of the amino-derivatized silica gel are preferably blocked by acylation with monocarboxylic acids such as acetic, benzoic or isobutyric acids, normally employing the acid anhydrides under acylating conditions.

The structure of the covalent linkage between the first nucleoside and the silica support is not critical as long as a substantially stable covalent linkage is formed to bind the nucleoside during the sequential nucleoside addition cycles. The covalent linkage therefore should be stable to the sequential reaction conditions but should be reasonably readily hydrolyzable to permit recovery of the formed oligonucleotide after completion of nucleoside addition. Thus, ester and amide linkages are particularly effective with the desired degree of stability and, at the same time, being readily hydrolyzable after nucleoside addition is completed using weak or strong bases.

As used herein the symbols for nucleotides and polynucleotides are according to the IUPAC-IUB Commission of Biochemical Nomenclature Recommendations [(1970) *Biochemistry* 9, 4022].

The following examples further illustrate the invention.

EXAMPLE 1

A. Polymer supports functionalized with carboxylic acid groups are prepared from silica gel.

A separation group silica gel supplied by Vydak as TP silica, having 20 μm particle size, 300 Å pore size is used as the starting material. The silica gel was placed in a desiccator over a saturated LiCl solution for 24 hours. The initial step in the process is silylation by refluxing 3-aminopropyltriethoxysilane (2.3 g, 0.01M) with the silica gel (2.6 g) in dry toluene. After silylation is substantially complete, in this case after about twelve hours of refluxing, the reaction mixture is cooled and the toluene solution removed. The thus silylated silica gel is then washed serially with toluene, ethanol and then with ether and air dried. Succinic anhydride (2.5 g, 0.025M) in water is next reacted with the silane modified silica gel to provide carboxylic acid functionality to the terminal portion of the covalently bonded silane side chains. During this latter reaction, the pH is maintained between 4 and 6 by addition of a base, such as 2N sodium hydroxide. After this latter reaction, which proceeded for about 6 hours, the modified silica gel containing carboxylic acid functional groups on its side chains is washed with water, then with methanol and ether, and then finally dried in vacuum at room temperature. The modified silica gel is then treated with trimethylsilylchloride [$(CH_3)_3SiCl$, 1.09 g, 0.01M] in anhydrous pyridine by refluxing for about 12 hours. The resulting modified silica gel is then washed with 5% trichloroacetic acid in water, then with water, and then with ethanol and ether. After drying in vacuum, the yield of carboxylic acid functionality on the modified silica gel is about 250 μmole/g.

B. 5'-O-dimethoxytrityldeoxythymidine (1.17 g, 0.002M) and the modified silica gel described in A (4 g, 0.001 mole carboxylic acid functional group) are reacted for about 40 hours in anhydrous pyridine using dicyclohexycarbodiimide (2.06 g, 0.01M) as condensing agent. The unreacted residual carboxylic acid groups in the modified silica are blocked, by the addition of p-nitrophenol (1.4 g, 0.01M) followed by the addition of 10% piperidine in pyridine (25 minutes). The reaction product is then washed serially with tetrahydrofuran, methanol and finally with ethyl ether. Then, as a precaution to assure complete blockage of unreacted carboxylic acid, the composition is first treated with dicyclohexylcarbodiimide and p-nitrophenol and then piperidine in pyridine for a second time. After removal of the dimethoxytrityl group using 0.1N p-toluenesulfonic acid in acetonitrile, the yield of thymidine attached to the support is found by spectrophotometry to be about 40 μmole/g.

The same procedure is used for attaching N-benzoyldeoxycytidine; N-benzoyldeoxyadenosine and N-isobutyryldeoxyguanosine. With purines, in this chemistry zinc bromide should be used to remove the trityl groups.

EXAMPLE 2

A. Silica gel (Vydac A, 25 gms) was placed in a desiccator over a saturated LiCl solution for 24 hr. The silica gel was transferred to a 500 ml round bottom flask, toluene (250 ml) and aminopropyltriethoxysilane (13 ml) were added, the flask was tightly sealed, and the suspension was gently shaken for 12 h at room temperature. The flask containing the suspended silica gel was next refluxed for 18 h. Before starting the reflux, add one boiling chip to the solution. Following the reflux step, the silica gel suspension was transferred to a centrifuge bottle and the silica gel pelleted by a low speed spin. The supernatant was decanted and the silica gel was washed with toluene (3×, 80 ml ea), methanol (3×, 80 ml ea) and methanol:H₂O, 1:1 (2×, 80 ml ea). The silica gel was next suspended in 80 ml 50% aqueous methanol and shaken overnight at room temperature. Once again the silica gel suspension was isolated by transfer to a centrifuge bottle followed by a low speed spin. The silica gel was next washed with methanol (2×, 80 ml ea) and ethyl ether (3×, 80 ml ea). Finally, the silica gel was air dried for 6 h and then dried in vacuo.

The silica gel was placed in a round bottom flask. A solution of dry pyridine (50 ml) and trimethylsilyl chloride was added and the suspension shaken at room temperature overnight. The silica was isolated by low speed centrifugation. The silica was then washed with methanol (5×, 80 ml) and ethyl ether (3×, 80 ml). The silica gel was air dried for 6 h and then dried in vacuo.

B. The 5'-O-dimethoxytrityl and N-protected deoxynucleoside (2.5 mole) was dissolved in a solution of dry pyridine (5 ml) and N,N-dimethylaminopyridine (0.3 g). Succinic anhydride (2.0 mmole, 0.2 g) was added and the solution stirred at room temperature for 12 h. Thin layer chromatography (tlc) in acetonitrile:water (9:1, v/v) can be used to monitor the reaction. Unreacted nuceloside will have an $R_f$ of approximately 0.8 whereas the product will be a smear from $R_f$ 0.3 to $R_f$ 0.5. After completion of the reaction, solvent is removed in a rotary evaporator and the dry gum is redissolved in toluene (10 ml). Toluene is removed using a rotary evaporator and the toluene co-evaporation procedure is repeated. The dry gum free of pyridine and N,N-dimethylaminopyridine is dissolved in methylenechloride (30 ml). This solution is transferred to an extraction funnel and 10% ice-cold citric acid is added. After vigorous shaking and extraction, the organic phase is washed twice with water (15 ml ea) and then dried over sodium sulfate. Approximately 0.3 ml pyridine is added to the methylene chloride solution in order to minimize detritylation while drying over sodium sulfate. The methylene chloride solution is concentrated to 10 ml and the succinylated nucleoside isolated by precipitation into hexane:ether (1:1, v/v; 250 ml). The precipitate is collected by centrifugation and dried in vacuo.

To obtain the nitrophenyl esters, succinylated nucleoside (1 mmole) was dissolved in dry dioxane (3 ml) containing pyridine (0.3 ml). DCC (10 mmole, 0.22 g) and p-nitrophenol (0.14 g, 1 mmole) were added and the solution shaken for 2 h. Dicyclohexyl urea was removed by centrifugation. Analysis by tlc in acetonitrile:H₂O (9:1, v/v) indicates the product with an $R_f$ of 0.8. This supernatant free of dicyclohexylurea is used directly for coupling to silica gel.

Silica gel prepared as outlined in A of this example, (5 g if 50 μmole nucleoside/g desired; 2.5 g if 100 μmole nucleoside/g desired) was suspended in dry DMF. Triethylamine (1 ml) was added free the silylamine from the hydrochloride salt. The p-nitrophenylsuccinylated nucleoside derivate (supernatant prepared herein) was added to the silica gel and the resulting suspension was shaken for two hours. An aliquot of silica gel (approx. 1 mg) was then removed for analysis. After washing the aliquot with DMF (2×), methanol (3×) and ethyl ether (2×), 0.1M toluenesulfonic acid in acetonitrile (1 ml) was added to the aliquot and the trityl released from silica as a red-orange color was observed. This analysis can be completed quantitatively if desired. If this analysis appears satisfactory (i.e. a positive trityl test), the bulk of the silica gel was washed with DMF (3×, 10 ml ea), dioxane (3×, 10 ml ea), methanol (5×, 10 ml ea), and ethyl ether (3×, 10 ml ea). Unreacted n-propylamino silyl groups were then blocked with a solution of acetic anhydride (0.7 ml) and dry pyridine (5 ml). The silica gel was isolated by centrifugation, decanting and repeated washing with methanol (4×, 10 ml ea) and ethyl ether (2×, 10 ml ea).

The assay for completeness of the capping or blocking of n-propylamino groups is as follows.

Take an aliquot (1 mg) of: (1) Underivatized Vydac-A, (2) Vydac derivatized with the aminopropyltriethoxysilane, (3) Vydac that has had nucleoside attached and subsequently blocked with acetic anhydride. Each sample was then treated with 250 μl of a saturated solution of sodium borate containing 0.2 mg/ml picryl sulfate. Vortex and centrifuge the reactant products. The underivatized Vydac should remain white. The aminopropylsilyl Vydac should appear bright orange-red. The capped Vydac will be pale yellow-orange. This is probably due to interaction of picryl sulfate with ring nitrogens on nucleosides.

With some preparations, a contaminant of succinylated n-propylamino groups will result from the presence of succinic acid. This succinic acid may be present because all the succinic anhydride was not consumed during the succinylation or alternatively was not removed as succinic acid during the aqueous extraction with citric acid. If succinylated n-propylamino groups are present, they can be blocked in the following manner. The protected silica gel containing succinylated nucleoside (either 5 g or 2.5 g) was suspended in a solution of dry pyridine (5 ml) containing DCC (0.28 g) and p-nitrophenol (0.16 g) and shaken overnight at room temperature. Morpholine (0.2 ml) was then added and the suspension shaken for 10 minutes. Silica gel was isolated after centrifugation, decantation of the supernatant, and washing the silica gel with methanol (4×, 10 ml ea), THF (3×, 10 ml ea) and ethyl ether (3×, 10 ml ea). After air drying, the silica gel was dried in vacuo.

A quantitative assay for the trityl cation and therefore the loading of nucleoside on the silica gel is as follows:
1. Weigh accurately approximately 1 mg of dry silica gel.
2. Add 1 ml of 0.1M toluenesulfonic acid in acetonitrile.
3. Measure the absorbance at 498 nm. If the absorbance approaches 2.0, dilute and re-read. The loading can be calculated as follows:

$$\text{loading in } \mu \text{ moles/g} = \frac{(\text{Abs}^{498})(\text{dilution factor})}{\text{wt silica gel in mg}} \times 14.3$$

If 5 gm silica gel was used, the loading should be approximately 40 μmole/g. If 2.5 gm silica gel was used, the loading will be approximately 100 μmole/g.

EXAMPLE 3

Deoxythymidine phosphomonochloridite is synthesized by the addition of 1.0 equivalent 5'-O-dimethoxytritylthymidine to 0.8 equivalent methylphosphorodichloridite and 5 equivalents collidine in THF at −78° C. The resulting compound and a thymine-modified silica gel matrix are utilized in oligonucleotide synthesis. The first step involves packing the thymidine-modified silica gel into a glass column. This column is attached through a series of valves and tubes to a pump and an injector loop. The apparatus is organized so that reagents can be recycled through the column, flushed to waste, or collected. The steps involved in synthesizing thymidylylthymidine attached to the support included:
(1) recycling the deoxythymidine phosphomonochloridite derivative in THF and collidine through the column of modified silica gel for about 1 hr; (2) oxidizing the polymer supported dinucleoside phosphite to the phosphate using 0.01M $I_2$ in water/2, 6 lutidine/THF (30 min); (3) recycling phenylisocyanate in THF and 2, 6 lutidine through the column for 1.5 hr. (this reagent protects against the formation of failure sequences by reacting with unphosphorylated nucleoside hydroxyl groups); (4) flushing the column with toluenesulfonic acid in acetonitrile (2 min). All steps were performed at room temperature. The total time needed for addition of one nucleotide, including various wash cycles after each step is about 4 hours. This four step procedure was repeated several times in order to produce good yields of two oligodeoxynucleotides, d(T)7 and d(T)9 attached to the silica gel matrix.

The same procedure as described above is used for preparing d(T-C-T-C-T-C-T-T-T). This cytosine containing phosphomonochloridite is prepared from 5'-O-dimethoxytrityl-N-benzoyldeoxycytidine.

EXAMPLE 4

Removal of Oligodeoxynucleotides from the Support and Characterization of the Compounds Produced The oligodeoxynuclotides [d(T)7, d(T)9, d(T-C-T-C-T-C-T-T-T)] are freed from protecting groups, isolated and characterized. The methyl group is removed from phosphotriesters using triethylammonium thiophenoxide in dioxane. This step is followed by treatment with concentrated NH4OH which removed the N-benzoyl group from cytosine and frees the oligonucleotides from the support. In each case the major product from each synthesis, as determined by high performance liquid chromatography, is found to be the described heptamer or the respective nonamers. Based on the amount of thymidine initially linked to the support, the isolated yield of d(T)9 is found to be about 25%. The corresponding yield of d(T-C-T-C-T-C-T-T-T) is found to be about 23%.

Both nonamers and the heptamer are also biochemically characterized. All three compounds are found to be completely degraded by Snake Venom Phosphodiesterase. The oligonucleotides isolated from each nonamer synthesis were phosphorylated using [5'-$^{32}$P]ATP and T4-kinase and then analyzed by gel electrophoresis before and after partial degradation with Snake Venom Phosphodiesterase. This analysis confirms that the oligonucleotide is homogeneous and contains nine nucleotide units. In order to confirm the sequence of [5'-$^{32}$P] d(pT-C-T-C-T-C-T-T-T), the sample is analyzed by two dimension homochromatography. The sequence profile is found to be consistent with the results expected for [5'-$^{32}$P] d(pT-C-T-C-T-C-T-T-T). Finally, [5'-$^{32}$P] d(pT)9 was shown to polymerize in the presence of T4-ligase and polydeoxyadenosine indicating that [5'-$^{32}$P]d(pT)9 forms a duplex with polydeoxyadenosine and that this duplex is recognized by T4-ligase. Therefore, d(T)9 and d(T-C-T-C-T-C-T-T-T) were biochemically active by every criteria so far tested.

In preferred embodiments, the amino groups, such as those on cytosine, adenine and quanine are protected. Protection of these groups is not a necessary part of this process but does enhance nucleoside solubilities in the appropriate solvents. Benzoyl, trityl (as previously defined herein) or isobutyryl groups provide suitable protecting groups, although other protecting groups can be used without altering this process. Protected nucleosides produced with good yields include 5'-O-dimethoxytrityl-deoxythymidine [DMTrd(T)], 5'-O-dimethoxytrityl-N-benzoyldeoxycytidine [DMTrd(bzC)], 5'-O-dimethoxytrityl-N-benzoyldeoxyadenosine [DMTrd(bzA)], and 5'-O-dimethoxytrityl-N-isobutyrl-deoxyguanosine [DMTrd(ibG)] as protected nucleosides. Protection of adenosine is preferable to avoid formation of side products which may require extensive aqueous hydrolysis for removal. A typical synthesis as illustrated with deoxyadenosine is as follows.

EXAMPLE 5

This example illustrates the use of purine deoxynucleotides.

DMTrd(bzA) (0.66 g., 1 mmole) in dry THF (3 ml) is added dropwise under an argon atmosphere to a stirred solution of the THF (3 ml) containing methyldichlorophosphite (0.113 ml, 1.2 mmole) and 2,4,6 trimethylpyridine (0.633 ml, 4.8 mmole) at −78° C. After 10 minutes at −78° C., the reaction solution is filtered through a sintered glass funnel and solvent is removed by concentration in vacuo. Excess methyl phosphodichloridite is removed by dissolving the resulting gum in toluene:THF (2 ml, 2:1) and re-evaporating in vacuo to a gum. This procedure is repeated several times to insure removal of the dichloridite. The nucleoside phosphomonochloridite is converted to the tetrazolide. The gum resulting from the final re-evaporation is dissolved in THF (2 ml). A solution of tetrazole (0.063 g, 0.9 mmole) in THF (2 ml) is then added dropwise with stirring at −78° C. to the nucleoside phosphomonochloridite. After 10 minutes at −78° C., the solution is transferred to a centrifuge tube, spun at low speed, and the supernatant is removed. This solution contains the activated nucleoside methylphosphomonotetrazolide. If not used immediately, this tetrazolide can be placed in long term storage after precipitation by dropwise addition into dry pentane, followed by collection, drying in vacuo, and storing in sealed tubes under argon or other inert gas at −20° C. All operations are performed under inert gas to avoid oxidation. At no time is the active agent exposed to air.

The foregoing procedure is applicable for the preparation of activated thymidine, deoxycytidine, and deoxyadenosine nucleotides. For the preparation of the activated deoxyguanosine nucleotide, the procedure is the same except for the stoichiometry. The molar ratio of DMTrd(ibG); methyldichlorophosphite; 2,4,6 trimethylpyridine and tetrazole is 1:0.9:3.8:0.7. The steps necessary for addition of one nucleotide to the modified silica gel polymer support follow. The removal of the dimethoxytrityl group from the nucleotide is accomplished by exposing the modified silica gel support to 0.1M $ZnBr_2$ in nitromethane for 15 to 30 minutes. The support is then washed initially with butanol: 2,6 lutidine:THF (4:1:5 by volume) and finally with THF. The solvent ratio is not important since this step is used to remove potential zinc esters of nucleosides. This step could be eliminated but lower yields may result. Other Lewis acids could be substituted for $ZnBr_2$, such as $BF_3$, $AlCl_3$ and $TiCl_4$. However $ZnBr_2$ is preferred. Protic acids can also be used. However approximately 3-5% depurination of each purine by protic acids is observed even when the amount of acid is reduced to the minimum amount needed to remove the dimethoxytrityl group. The next step in the process is condensation of the protected and activated nucleotide to the nucleoside or oligonucleotide covalently bound to the support. This is accomplished by using 10-15 equivalents of the activated monotetrazolide and a reaction time of about one hour. The solvent is anhydrous THF. This process may also be used for the addition of the activated monochlorides, triazolides and nitroimidazolides. However, best results were obtained with the tetrazolide. The next step in the process is the blocking of unreacted 5'-hydroxyl groups. This is accomplished using a solution of acetic anhydride, dimethylaminopyridine, pyridine and THF. This may also be accomplished using a 0.33M solution of diethylmonotriazolephosphite in 2.6-lutidine/THF (1:5 by volume). The reaction time is 5 minutes and is followed by a THF wash. As a further alternative, a solution of phenylisocyanate/lutidine (45:55 by volume) and a 90 minute reaction time may be used for this step. This solution is then removed from the modified silica gel by washing the support with THF and with acetonitrile. The first procedure is preferred. This step can be eliminated or other reagents that react with 5'-hydroxyl groups and are compatible with the overall chemistry can be substituted therefor. However, by including this step, the final purification of the desirable oligonucleotide is rendered much easier. This is because the complexity of the total synthetic material bound to the support is reduced considerably. The final step in each cycle is oxidation of the phosphite to the phosphate. A composition of 0.1M $I_2$ in water/2,6lutidine/THF (1:1:3) is preferred, although other ratios can be used. Furthermore, other oxidizing agents such as N-chlorosuccinimide or aryl or alkyl peroxides could also be used. Iodine is presently preferred as oxidizing agent. After the addition of the appropriate activated nucleotides in any predetermined sequence, the deoxyoligonucleotide is removed from the support as described above in the synthesis of $d(T)_9$.

The compounds of formula II herein in which X is a secondary amino group formed by removal of the H atom of the secondary amino nitrogen of a nitrogen heterocyclic compound are new compounds which are particularly useful in forming the requisite phosphorus linkage. These compounds are more reactive and consequently more efficient than the corresponding compounds wherein X is halogen. These compounds are readily prepared from the compounds in which X is halogen (as described, for example, in Example 5) or can be formed by reaction of a halo-(2° amino)-alkoxyphosphine with the selected nucleoside.

The use of such heterocyclicaminophosphine compounds is exemplified in the succeeding examples, particularly example 5 which illustrates the preparation of a tetrazolide and use thereof in forming the necessary phosphorus linkage.

Employing this procedure, a variety of such compounds are prepared using tetrazole, nitroimidazole and triazole as well as various nucleosides to obtain the corresponding nucleoside phosphonomonamine. Particularly, such compounds include as nucleoside base thymine, cytosine, adenosine and guanine and such compounds are further protected with blocking groups as required, e.g. benzoyl groups on the amino group of cytosine and adenine as well as isobutyryl or the amino group of quanine.

EXAMPLE 6

A. HPLC grade silica gel (2 g, Vydac Tp-20, Separation Group, 100 $m^2/g$ surface area, 300 Å pore size, 20 m particle size) was exposed to a 15% relative humidity atmosphere satd. LiCl) for at least 24 h. The silica (2.0 g) was then treated with 3-triethoxysilylpropylamine (2.3 g, 0.01M in toluene for 12 h at 20° and 12 h at reflux under a Drierite drying tube. This reaction was completed on a shaking apparatus because magnetic stir bars pulverize the silica gel and should be avoided. The silica was isolated by centrifugation, washed successively (twice each) with toluene, methanol and ether and air dried.

B. The carboxylic acid group was introduced by agitating the silica so produced (2 g) and succinic anhydride (2.5 g, 0.025M) in water. The pH was controlled (pH 2-6) by addition of 2M NaOH. Completeness of the carboxylation reaction was qualitatively monitored using a picrate sulfate test. An aliquot of silica (approximately 2 mg) was treated with 0.5 ml of 0.1M picrate sulfate in saturated sodium borate buffer (pH 10). The original silica reacted within 10 min and stained a bright yellow whereas the acylated product remained white.

The succinic anhydride reaction was allowed to continue until the silica gel remained white during the picrate sulfate test. Usually the total reaction time was one hour and a second addition of succinic anhydride was required. After washing successively (twice each) with water, 0.1M trichloroacetic acid, water, methanol and ether, compound 2 was air dried, dried in vacuo, and then treated with trimethylsilylchloride (1.25 ml, 0.01M) in pyridine (7 ml) for 24 h at 25° and the product was then washed with methanol (4 times) and ether. Analysis for extent of carboxylation involved a two step procedure. An accurately weighed aliquot was treated with dicyclohexylcarbodiimide (DCC) and p-nitrophenol in pyridine. After several washings with tetrahydrofuran to remove unreacted p-nitrophenol, 10% piperidine in pyridine was added to the silica gel and the amount of p-nitrophenol released was measured at 410 nm using $1.57 \times 10^4$ as the extinction coefficient of p-nitrophenoxide. The incorporation of carboxylic acid was 200 μmol/g.

C. The deoxynucleosides were joined to this product using DCC. 5'-O-dimethoxytritylthymidine (1.1 g, 2.16 mmol) DCC (2 g, 0.01 mol), and 2 (4 g, 0.8 mmol carboxylic acid) were agitated in dry pyridine (21 ml) for 2 days. P-Nitrophenol (1.4 g, 0.01 mol) was added, the mixture was agitated for an additional day, and then the reaction was quenched with morpholine (1 ml, 0.011 mol). After washing with methanol and ether, the silica gel was analyzed for unreacted carboxylic acid. Usually a second treatment with DCC (2 g, 0.01 mol) and p-nitrophenol (1.4 g, 0.01 mol) in dry pyridine (20 ml) and finally morpholine (1 ml) was necessary to completely block the trace amount of free carboxylic acid (<10 μmol/g) that remains from the first blocking procedure.

5'-O-Dimethoxytritylthymidine, 5'-O-dimethoxytrityl-N-benzoyldeoxycytidine, 5'-O-dimethoxytrityl-N-isobutyryldeoxyguanosine and 5'-O-dimethoxytrityl-N-benzoyldeoxyadenosine were converted to activated nucleoside by introduction of the requisite phosphinyl chloride group using the following procedure.

5'-O-Dimethoxytritylthymidine (1.6 g, 2.9 mmol) in anhydrous tetrahydrofuran (5 ml) was added dropwise to a well stirred solution at −78° of $CH_3OPCl_2$ (0.33 ml, 2.5 mmol) and collidine (1.86 ml, 14.1 mmol) in anhydrous tetrahydrofuran (5 ml). A white precipitate formed during the addition. The mixture was stirred for 15 min at −78° and then filtered through a sintered glass funnel to remove collidine hydrochloride. The collidine hydrochloride was washed with dry tetrahydrofuran (1 ml). The filtrate was then diluted with dry toluene and concentrated to a gum. After dry argon had been bled into the apparatus, a solution (6 ml) containing toluene:tetrahydrofuran (2:1) was added and the gum was allowed to dissolve completely in this solution. Solvent was removed by concentration in vacuo. This reconcentration using a solution of toluene and tetrahydrofuran was repeated three times. After the final concentration, the gum was dissolved in dry tetrahydrofuran (3 ml), cooled to −78° and a solution of tetrazole (0.18 g, 2.6 mmol) in dry tetrahydrofuran (3 ml) was added dropwise. A white precipitate of collidine hydrochloride formed during the addition. The mixture was stirred an additional 10 min at −78° and then transferred using positive argon pressure and a cannula to a centrifuge tube filled with argon. The supernatant recovered after centrifugation contained the tetrazolylphosphite product which can be used directly for synthesis of deoxyoligonucleotides. Alternatively, the tetrazolylphosphite can be stored as a precipitate and reconstituted as needed.

5'-O-dimethoxytrityl-N-benzoyldeoxyadenosine (1.91 g, 2.9 mmol) is substituted for 5'-O-dimethoxytritylthymidine to obtain the corresponding deoxyadenosine compound.

The aforesaid phosphites, i.e. activated nucleotides, were used in the synthesis of deoxyoligonucleotides in an automated apparatus in accordance with the accompanying drawing.

Synthesis of deoxyoligonulceotides. The apparatus consists of a Milton Roy Minipump, three way Altex slide valves, a recycle valve (a modified Altex valve) and an injector loop (a three way Altex valve). All connections were with teflon tubing and were designed to minimize the tubing volume in the recycle loop. The column was an 11 mm Ace glass column that had been shortended to approximately 1 ml capacity. Cellulose filters were used to support the silica bed. The filters were acetylated with a solution of acetic anhydride and pyridine (1:1 based on volume) for 4 h at 50° before use. The total volume contained within the recycle loop of this apparatus was approximately 2.5 ml. The tetrahydrofuran reservoir was protected from air with a nitrogen bubbler and the $ZnBr_2$ solution was protected from moisture with the Drierite tube.

The various chemical operations that must be performed for the addition of one nucleotide to the silica are listed in Table Ia.

TABLE Ia

Protocol for Machine Assisted Polynucleotide Synthesis

| Reagent or Solvent[a,b] | Time (min) | Machine Mode |
|---|---|---|
| Satd. $ZnBr_2/CH_3NO_2$ | 30 | Flush |
| $CH_3(CH_2)_2CH_2OH$/2,6-lutidine/THF | 5 | Flush |
| THF | 10 | Flush |
| Activated Nucleotide | 60 | Recycle |
| $(CH_3CH_2O)_2P$ (triazole) | 5 | Recycle |
| THF | 2 | Flush |
| $I_2$ Oxidation | 5 | Flush |
| THF | 5 | Flush |
| $CH_3NO_2$ | 3 | Flush |

[a]THF, Tetrahydrofuran
[b]A nitromethane solution saturated with $ZnBr_2$ is approximately 0.1 M in $ZnBr_2$ Typically, 0.25 g of nucleoside/silica gel (10 μmole nucleoside) was loaded into the column and the silica washed with nitromethane. The 5'-O-dimethoxytrityl group was removed by flushing the column (30 min) with nitromethane saturated with $ZnBr_2$ (approximately 0.1M in $ZnBr_2$) at a pump speed of 1 ml/min. The completeness of deprotection was monitored visually or spectrophotometrically by observing the release of a bright orange dimethoxytrityl cation. By measuring the absorbance at 498 nm, the completeness of the previous condensation step was monitored. This step was followed successively by a wash with a solution of n-butanol:2,6-lutidine:tetrahydrofuran (4:1:5) for 5 min at a flow rate of 2 ml/min. The next step was a wash for 5 min (5 ml/min) with dry tetrahydrofuran. During the course of this washing step, the recycle valve and the injector port were also flushed with dry tetrahydrofuran and the effectiveness of this wash was monitored at 254 nm using a spectrophotometer. The condensation step was next completed using activated nucleotide that had been reconstituted using dry tetrahydrofuran. The reconstituted solution was stored in a dry ice/acetone bath over argon but condensation reactions were carried out at room temperature. When reconstituted, activated nucleotide stored in this way was stable for several days. Approximately 10 equivalents of activated nucleotide (100 μmole for 0.25 g of nucleoside/silica gel) in 0.5 to 0.8 ml of tetrahydrofuran was injected into the apparatus and the machine switched to the recycle mode. The activated nucleotide was circulated through the silica gel for 1 h at a pump speed of 2 ml/min. Aliquots of activated nucleotide from the apparatus were then collected directely into dry methanol and water. Analysis as described previously indicated whether activated nucleotide was still present in the system. Usually this is the case. However, occasionally (approximately 1 in 10) the bis methyl phosphite of the deoxynucleotide was not observed by this assay. When this occurred, the condensation step was repeated to prevent the possibility of incomplete reaction. The next step involves capping unreacted 5'-O-hydroxyls by adding diethoxytriazoylphosphine (1 ml of a 0.3M solution in tetrahydrofuran) directly to the solution of activated nucleotide and continuing the recycle mode for 5 min at a pump speed of 2 ml/min. Residual activated nucleotide and the capping reagent were then flushed from the apparatus using dry tetrahydrofuran (2 min at 5 ml/min). This step was followed by oxidation of phosphites using a solution of tetrahydrofuran:2,6-lutidine:-water (2:1:1) containing 0.2M $I_2$. The solution was flushed through the apparatus for 5 min (2 ml/min). Finally the cycle was completed by flushing the system first with dry tetrahydrofuran for 3 min (5 ml/min) and nitromethane for 2 min(5 ml/min). This cycle is then repeated an appropriate number of times to complete the desired sequence.

Isolation of Deoxyoligonucleotides. The completely deprotected deoxyoligonucleotides were isolated by the following procedure. An aliquot (10 mg) of the silica gel containing the deoxyoligonucleotide triester in protected form was first treated with thiophenol:triethylamine:dioxane (1:1:2, v/v). After 45 min of gentle shaking, the silica gel was recovered by centrifugation and washed with methanol (4 times) and ethyl ether. After air drying, the deoxyoligonucleotide was removed from the support by a three hour treatment with concentrated ammonium hydroxide at 20° followed by centrifugation. Base protecting groups were removed by warming the supernatant at 50° for 12 h in a sealed tube. The 5'-O-dimethoxytrityldeoxyoligonucleotide was isolated by concentrating the hydrolysate in vacuo, dissolving the residue in 0.1M triethylamminium acetate (ph 7.0) and chromatographing this material on a $C_{18}$ reverse phase hplc column (Waters Associates). The eluting buffer was 0.1M triethylammonium acetate containing 26% acetonitrile. The peak containing 5'-O-dimethoxytrityldeoxyoligonucleotide was concentrated in vacuo and the residue was treated at 20° for 15 min with acetic acid-water (4:1, v/v) to remove the 5'-O-dimethoxytrityl group. The completely deprotected deoxyoligonucleotide was isolated by concentration of the acetic acid solution in vacuo, dissolving the residue in 25 mM triethylammonium bicarbonate (pH 7), and extraction of dimethoxytritanol with water saturated ether.

Characterization of Deoxyoligonucletotides. The 5'-hydroxyl of each deoxyoligonucleotid was phosphorylated using [5'-$^{32}$P]ATP and $T_4$-kinase. The amount of deoxyoligonucleotide used in a phosphorylation reaction was determined by measuring the absorbance and using a calculated extinction coefficient which assumed no hypochromicity for the deoxyoligonucleotide. Phosphorylated deoxyoligonucleotides were separated from excess ATP by desalting on a G-50-40 Sephadex column using 10 mM triethylammonium bicarbonate (pH 7) as eluant. Gel electrophoresis on polyacrylamide and two dimension analysis were completed using standard procedures.

Synthesis of d(C-G-T-C-A-C-A-A-T-A). Silica gel modified with 5'-O-dimethoxytritylthymidine (0.25 g, 50 μm/g) was loaded into the column and the cycle was started by washing the silica gel with nitromethane and removing the 5'dimethoxytrityl group with $ZnBr_2$. Elongation was performed as previously described using an approximate tenfold excess of the incoming activated nucleoside phosphite (0.1 mM) at each condensation. Synthesis was continued to the completion of the deoxyoctanucleotide, d(T-C-A-C-A-A-T-T). At this point the silica was divided into two approximately equal portions. One portion was elongated to the deoxydecanucleotide in standard fashion. The overall yield was 64% based on the amount of dimethoxytrityl group bound to the support and 30% was the yield isolated from a reverse phase hplc column.

Synthesis of d(A-C-G-C-T-C-A-C-A-A-T-T). The remaining portion of d(T-C-A-C-A-A-T-T) was elongated in standard fashion in the machine to the deoxydodecanucleotide. The overall yield was 55% based on the dimethoxytrityl group bound to the support. The isolated yield was not accurately determined.

The following oligonucleotides were prepared using the procedures described:
5'-d(A-A-T-T-C-A-C-C-G-T-G)
5'-d(C-G-T-G-T-T-G-A-C-T)
5'-d(A-T-T-T-T-A-C-C-T-C-T)
5'-d(G-G-C-G-G-T-G-A-T-A)
5'-d(A-T-G-A-G-C-A-C)
5'-d(A-A-T-T-G-T-G-C)
5'-d(T-C-A-T-T-A-T-C-A)
5'-d(C-C-G-C-C-A-G-A-G)
5'-d(G-T-A-A-A-A-T-A-G-T-C-A)
5'-d(A-C-A-C-G-C-A-C-G-G-T-G)

The procedures described in the foregoing examples can also be used for synthesizing mixed nucleoside and deoxynucleoside oligonucleotides by the simple expediency of inserting the desired nucleoside moiety at the desired point in the sequence. Thus, the present process, in addition to being useful for production of oligonucleotides of natural sequence of the individual nucleosides, can be used to produce synthetic oligonucleotides hitherto unknown in natural occurence which can be useful in research and synthesis of polynucleotides, and eventually genes for use in biological systems.

A particularly preferred embodiment of the present invention is the detritylation of the 5'-O trityl nucleosides, deoxynucleotides, oligonucleotides, oligodeoxynucleotides, polynucleotides and polydeoxynucleotides using a Lewis acid, particularly zinc bromide, although other Lewis acids can also be employed, e.g. titanium tetrachloride. The use of Lewis acids is superior to the use of protic acids for removal of the trityl group from the 5'-O-position since reaction is extremely fast and is not accompanied by depurination. The process is also specific for 5'-O-trityl and thus provides a very practical procedure to permit production of 3'-O-trityl blocked nucleosides by reaction with the 3'-O and 5'-O ditritylated compound.

The procedure merely requires contacting the reactants preferably in a reaction solvent and detritylation occurs within short reaction times. The Lewis acid is normally suspended in the reaction solvent and the solvent is usually water-free to prevent reaction with the Lewis acid to form protic acids. In present experience, nitromethane is the preferred solvent although a variety of other solvents can be used, e.g. dioxane and tetrahydrofuran and mixtures of such solvents with each other and other solvents such as acetone, methylene chloride, and the like.

The rate of detritylation was measured and comparative data is provided in Table II.

TABLE II

The Rate of Detritylation and Depurination of 5'-Dimethoxytrityl-N—benzoyldeoxyadenosine Using Various Solutions*

| Solution | Temp. | Detritylation Time | % | Depurination Time | % |
|---|---|---|---|---|---|
| satd. $ZnBr_2/CH_3NO_2$** | 18° C. | <1 min | 100 | 10 hrs | 50 |
| satd. $ZnBr_2/CH_3NO_2$ | 0° C. | 10 min | 100 | 21 hrs | <5 |
| 2% toluenesulfonic acid/ $CHCl_3:CH_3OH$ (7:3) | 18° C. | <1 min | 100 | 5 min | 50 |
| 0.5% toluenesulfonic acid/$CHCl_3:CH_3OH$ (7:3) | 0° C. | 10 min | 100 | 8 hrs | 50 |

*All depurination results summarized in this communication were obtained by analyzing reaction mixtures using reverse phase high pressure liquid chromatography. Estimates of detritylation times were by thin layer chromatography.
**A nitromethane solution saturated with $ZnBr_2$ is approximately 0.1 M in $ZnBr_2$.

The results obtained with various tritylthymidines at room temperature with zinc bromide is give in Table III.

TABLE III

The Rate of Detritylation and Degradation of 5'-Trityldeoxynucleosides Using $ZnBr_2$ at Room Temperature

| Deoxynucleoside | Detritylation Time | % | Degradation Time |
|---|---|---|---|
| 5'-Dimethoxytrityl-N—isobutynyldeoxyguanosine | <1 min | 100 | 50 hrs |
| 5'-Dimethoxytrityl-N—benzoyldeoxycytosine | <1 min | 100 | 24 hrs |
| 5'-Dimethoxytritylthymidine and at 0° C. in Table IV. | <1 min | 100 | 24 hrs |

TABLE IV

The Rate of Detritylation of Various Tritylthymidines Using Saturated $ZnBr_2$ in Nitromethane at 0° C.

| Nucleoside | Time | % Detritylation |
|---|---|---|
| 5'-Dimethoxytritylthymidine | 1 min | 50 |
| 5'-Monomethoxytritylthymidine | 1 min | 50 |
| 5'-Tritylthymidine | 10 min | 50 |
| 3'-Monomethoxytritylthymidine | 30 min | 10 |

The detritylation procedure is not restricted to polymer support synthesis but is also useful for strictly solution synthesis procedures where the use of trityl groups is included in the reaction sequence.

Of particular value as blocking groups definitive of R are arylmethyl groups, including monoaryl dialkylmethyl, diaryl monoalkylmethyl and triarylmethyl blocking groups. Of these, the preferred are the triarylmethyl of which the trityl blocking groups are well known. The triarylmethyl blocking groups are generally readily removable but they also afford a method of monitoring the sequencing of oligonucleotides as well as the yield of product obtained. One major criticism of known oligonucleotide synthesis is the lack of monitoring of the product produced in successive condensations of nucleotides. Such monitoring would require removal of an aliquot of the reaction system, e.g. the silica gel or other support on which the oligonucleotide is being synthesized, hydrolysis of the product from the support and finally analysis of the product, all of which is time-consuming. Because of this difficulty, oligonucleotides are usually synthesized without appropriate monitoring steps which is most undesirable. The use of triarylmethyl blocking groups provides a simple but accurate method of monitoring the sequence of nucleosides in the oligonucleotide product as formed, as well as the yield of product obtained at each stepwise addition of nucleoside.

This method is predicated on color formation by the triarylmethyl cation in the presence of an acid, whether a Lewis acid or a protic acid. By selection of appropriate triarylmethyl blocking groups for the phosphoramidite compound of structures II or IIa herein, which provide distinguishing color in acids, each nucleoside can be labelled with the triarylmethyl group of distinguishing color. As each condensation reaction is completed to form the phosphorus linkage illustrated in compounds of formula III and IIIa herein, the next step in the synthesis is the removal of the blocking group R therefrom. This is conveniently accomplished with a Lewis acid such as zinc bromide and simultaneously produces a color reaction, e.g. di-p-anisylphenylmethyl group forms an orange color with $ZnBr_2$, when removed from the oligonucleotide. The color can be used to identify the triarylmethyl blocking group used to identify the initial phosphoramidite employed and also to measure the extent of reaction by measurement of the intensity thereof.

Most triarylmethyl groups, in present experience, have shown color production on exposure to acids. In fact, a wide variety of colors has been obtained by varying the make-up of the triarylmethyl group, including as the aryl group not only phenyl and naphthyl but also substituted phenyl and naphthyl, as well as heterocyclic rings such as quinolinyl, furyl, thienyl, and other nitrogen, sulfur and/or oxygen containing heterocyclic rings. The said aryl groups can include substituents such as halide (F, Cl, Br, I); nitro, alkoxy, alkyl, aryl, aralkyl, cycloalkyl and like hydrocarbyl substituents. In these substituents, the number of carbon atoms should preferably be from 1 to about 12.

The preferred triarylmethyl groups are represented by the formula:

wherein each of $R_1$, $R_2$ and $R_3$ is an aryl group such as phenyl, naphthyl, quinolyl, furyl, thienyl, or other nitrogen, sulfur and/or oxygen-containing heterocyclic ring; or such aryl groups with a monosubstituent such as halide (F, Cl, Br or I), nitro, lower alkoxy, lower alkyl, and aryl, aralkyl and cycloalkyl containing up to 10 carbon atoms. $R_2$ and $R_3$ each may also be alkyl, cycloalkyl or aralkyl containing up to 10 carbon atoms.

Preferable triarylmethyl groups are given in Table V.

TABLE V

LEGEND

TABLE V-continued
LEGEND

| Aryl Functional Groups as Defined in the Legend | Color |
|---|---|
| $R_1 = R_2 = c; R_3 = a$ | Orange |
| $R_1 = c; R_2 = b; R_3 = a$ | Red |
| $R_1 = c; R_2 = d; R_3 = a$ | Orange |
| $R_1 = c; R_2 = q; R_3 = a$ | Colorless |
| $R_1 = c; R_2 = r; R_3 = a$ | Colorless |
| $R_1 = c; R_2 = p; R_3 = a$ | Red-Orange |
| $R_1 = R_2 = b; R_3 = a$ | Black |
| $R_1 = R_2 = q; R_3 = a$ | Colorless |
| $R_1 = R_2 = r; R_3 = a$ | Colorless |
| $R_1 = R_2 = p; R_3 = a$ | Violet-Red |
| $R_1 = R_2 = a; R_3 = c$ | Yellow-Orange |
| $R_1 = R_2 = a; R_3 = b$ | Yellow |
| $R_1 = R_2 = a; R_3 = d$ | Yellow |
| $R_1 = R_2 = a; R_3 = q$ | Colorless |
| $R_1 = R_2 = a; R_3 = r$ | Colorless |
| $R_1 = R_2 = c; R_3 = n$ | Violet |
| $R_1 = R_2 = b; R_3 = n$ | Blue |
| $R_1 = R_2 = p; R_3 = n$ | Deep Purple |
| $R_1 = R_2 = c; R_3 = o$ | Burnt-Orange |
| $R_1 = R_2 = c; R_3 = p$ | Purple |
| $R_1 = R_2 = b; R_3 = p$ | Purple |
| $R_1 = R_2 = g; R_3 = m$ | Yellow-Orange |
| $R_1 = R_2 = f; R_3 = m$ | Colorless |
| $R_1 = R_2 = p; R_3 = m$ | Peach |
| $R_1 = R_2 = e; R_3 = m$ | Yellow |
| $R_1 = R_2 = d; R_3 = m$ | Yellow |
| $R_1 = R_2 = c; R_3 = m$ | Yellow |
| $R_1 = R_2 = a; R_3 = m$ | Colorless |
| $R_1 = R_2 = b; R_3 = m$ | Lilac |
| $R_1 = R_2 = g; R_3 = c$ | Red-Orange |
| $R_1 = R_2 = f; R_3 = c$ | Yellow |
| $R_1 = R_2 = p; R_3 = c$ | Red |
| $R_1 = R_2 = e; R_3 = c$ | Red-Orange |
| $R_1 = R_2 = d; R_3 = c$ | Red |
| $R_1 = R_2 = R_3 = c$ | Red |
| $R_1 = g; R_2 = a; R_3 = i$ | Deep Red |
| $R_1 = f; R_2 = a; R_3 = i$ | Yellow |
| $R_1 = p; R_2 = a; R_3 = i$ | Yellow |
| $R_1 = e; R_2 = a; R_3 = i$ | Red-Violet |
| $R_1 = d; R_2 = a; R_3 = i$ | Burnt-Orange |
| $R_1 = c; R_2 = a; R_3 = i$ | Deep Purple |
| $R_1 = R_2 = a; R_3 = i$ | Red-Violet |
| $R_1 = b; R_2 = a; R_3 = i$ | Red |
| $R_1 = g; R_2 = a; R_3 = j$ | Yellow |
| $R_1 = f; R_2 = a; R_3 = j$ | Yellow |
| $R_1 = p; R_2 = a; R_3 = j$ | Colorless |
| $R_1 = e; R_2 = a; R_3 = j$ | Orange |
| $R_1 = d; R_2 = a; R_3 = j$ | Carmine |
| $R_1 = c; R_2 = a; R_3 = j$ | Deep Burnt Orange |
| $R_1 = R_2 = a; R_3 = j$ | Yellow |
| $R_1 = R_2 = g; R_3 = k$ | Yellow |
| $R_1 = R_2 = f; R_3 = k$ | Yellow |
| $R_1 = R_2 = p; R_3 = k$ | Colorless |
| $R_1 = R_2 = e; R_3 = k$ | Yellow-Orange |
| $R_1 = R_2 = d; R_3 = k$ | Yellow |
| $R_1 = R_2 = c; R_3 = k$ | Orange |
| $R_1 = R_2 = a; R_3 = k$ | Yellow |
| $R_1 = g; R_2 = R_3 = a$ | Yellow |
| $R_1 = f; R_2 = R_3 = a$ | Yellow |
| $R_1 = p; R_2 = R_3 = a$ | Yellow |
| $R_1 = e; R_2 = R_3 = a$ | Orange |
| $R_1 = R_2 = R_3 = a$ | Yellow |
| $R_1 = n; R_2 = l; R_3 = a$ | Green |
| $R_1 = h; R_2 = l; R_3 = a$ | Canary Yellow |
| $R_1 = g; R_2 = l; R_3 = a$ | Yellow |
| $R_1 = c; R_2 = l; R_3 = a$ | Yellow Orange |
| $R_1 = n; R_2 = g; R_3 = a$ | Green |
| $R_1 = h; R_2 = g; R_3 = a$ | Canary Yellow |
| $R_1 = R_2 = g; R_3 = a$ | Yellow |
| $R_1 = c; R_2 = g; R_3 = a$ | Yellow-Orange |
| $R_1 = b; R_2 = g; R_3 = a$ | Yellow |
| $R_1 = n; R_2 = R_3 = g$ | Green |
| $R_1 = h; R_2 = R_3 = g$ | Canary Yellow |
| $R_1 = R_2 = R_3 = g$ | Yellow |
| $R_1 = b; R_2 = R_3 = g$ | Yellow |
| $R_1 = n; R_2 = j; R_3 = a$ | Green |
| $R_1 = h; R_2 = j; R_3 = a$ | Canary Yellow |
| $R_1 = g; R_2 = j; R_3 = a$ | Yellow |
| $R_1 = c; R_2 = j; R_3 = a$ | Yellow-Orange |
| $R_1 = n; R_2 = R_3 = a$ | Green |
| $R_1 = h; R_2 = R_3 = a$ | Yellow |
| $R_1 = a; R_2 = e; R_3 = n$ | Green |
| $R_1 = a; R_2 = e; R_3 = h$ | Yellow |
| $R_1 = a; R_2 = e; R_3 = g$ | Yellow |
| $R_1 = a; R_2 = e; R_3 = c$ | Yellow-Orange |
| $R_1 = a; R_2 = c; R_3 = n$ | Red |

All colors were determined by the following procedure: an aliquot of the hydrolyzed Grignard reaction product (the triarylmethyl alcohol produced by the procedure described in Example V herein) was analyzed by thin layer chromatography. The thin layer plates were then exposed to hydrochloric acid vapor and the color of the trityl cations recorded.

Thus, of the blocking groups definitive of R, the preferred are the arylmethyl groups, particularly triarylmethyl groups, and especially those arylmethyl groups which provide a visible color when contacted with acids.

The following examples further illustrate the use of color coding in the present invention.

EXAMPLE VII

General method for synthesizing chlorotriarylmethanes

In the synthesis of this series of compounds there are two types of substrates for the respective Grignard reagents: (1) diaryl ketones, i.e. benzophenones, which require one equivalent of Grignard reagent; (2) esters of aryl carboxylic acids, which require two equivalents. The following will describe the former. Appropriate adjustments should be made for reactions of the latter type.

TABLE VI

A Summary of Reagents Used for Synthesizing Triarylcarbinols

| Reagent | Example | mmoles |
|---|---|---|
| aryl bromide | p-bromoanisole | 100 |
| magnesium | | 110 |
| diethyl ether | | 250 ml |
| iodine | | 2 crystals |
| diaryl ketone | 4-methoxybenzophenone | |

The magnesium, aryl bromide and ether are combined in 1000 ml round bottom flask. The iodine is added. In order to initiate the formation of the aryl magnesium bromide, it is necessary to crush the magnesium with a glass rod. [Note: grinding the magnesium in a Waring Blender also helps to get the reaction going.] Once the reaction has begun, it is allowed to reflux, with no external heating, until the ether ceases to boil. An ethereal solution of the diarylketone is added dropwise, with stirring. The reaction is allowed to proceed overnight. At this time the reaction is analyzed by thin layer chromotography (tlc) in 1:1 ether:hexane. The $R_f$ of the product will be approximately 0.7.

If the reaction is satisfactory, it is quenched with 10% (w/v) ammonium sulfate. The product is extracted four times with 300 ml of toluene. The extracts are dried over sodium sulfate and evaporated down as far as possible. The concentrated organic phase is dried in vacuo overnight. At this time the product crystallizes out. The product tritanol is collected in a funnel and washed with hexane.

The tritanol is taken up in 100 ml of toluene. 200 mmoles of acetyl chloride is added. 300 ml of hexane is added. The product is allowed to recrystallize overnight at $-20°$ C. The crystals are collected, washed with hexane, and dried in vacuo.

In order to determine the reactivity of the trityl chloride, a small amount is quenched into water and N-butanol with toluene as solvent. The samples are analyzed via tlc using 3:1 hexane:ether. The trityl butyl ether runs at $R_f$ approximately 0.8 while the tritanol runs at $R_f$ approximately 0.4.

Using this procedure, the various alcohols described in Table I were prepared.

Several of the triarylmethylchlorides were condensed with the 5' hydroxyl of appropriately protected deoxynucleosides. These compounds are listed in Tables VII and VIII. The 5'-triarylmethyldeoxynucleosides were treated with protic and Lewis acids using carefully controlled conditions. The results of these studies are also recorded in Tables VII and VIII. These results show that several triarylmethyl groups forming different colors in acid solutions are hydrolyzed at approximately the same rapid rate in the presence of $ZnBr_2$. The rates are more variable with protic acids.

TABLE VII

The Lewis Acid Hydrolysis Rates of Triarylmethyl Groups Attached to the 5'-Hydroxyl of Deoxynucleosides[1]

| Triarylmethyl Group[2] | Deoxy-nucleoside[3] | $t_{\frac{1}{2}}$ (sec) in $ZnBr_2$ | Color in Acid |
|---|---|---|---|
| $R_1 = n; R_2 = c; R_3 = a$ | T | 60 | Green |
| $R_1 = n; R_2 = e; R_3 = a$ | T | 60 | Red |
| $R_1 = R_2 = c; R_3 = a$ | T | 60 | Orange |
| $R_1 = R_2 = b; R_3 = n$ | T | 30 | Blue |
| $R_1 = R_2 = c; R_3 = a$ | C | 45 | Orange |
| $R_1 = R_2 = b; R_3 = n$ | C | 30 | Blue |
| $R_1 = R_2 = b; R_3 = a$ | G | 20 | Black |
| $R_1 = R_2 = c; R_3 = a$ | G | 20 | Orange |
| $R_1 = h; R_2 = R_3 = a$ | A | 45 | Yellow |
| $R_1 = R_2 = c; R_3 = a$ | A | 20 | Orange |

[1] Reaction conditions were 0.08 M $ZnBr_2$ in nitromethane. Aliquots were removed from the reaction solution, quenched with ammonium acetate and analyzed visually after tlc and exposure to HCl vapors. Time points were taken at 10, 20, 30, 45, 60, 90, 120, 180, and 240 sec.
[2] The aromatic functional groups are defined in the legend to Table I.
[3] The symbols T, C, G and A refer to the nucleosides thymidine, N—benzoyldeoxycytidine, N—isobutyrldeoxyguanosine, and N—benzoyldeoxyadenosine. The nucleoside 5'-hydroxyl was derivatized to contain the triarylmethyl group.

For the repetitive addition of mononucleotides to a growing oligonucleotide attached covalently to a polymer support, the various color coded triarylmethyl groups should preferably be hydrolyzed at approximately the same rate. Otherwise, each addition cycle must be individually monitored if completed manually or independently programmed if completed in a machine. Because the hydrolysis rates with $ZnBr_2$ are similar, the results outlined in Table VII suggest that most, if not all, of the triarylmethyl alcohols listed in Table 1 could be incorporated into synthetic procedures as color coded blocking groups.

TABLE VIII

The Protic Acid Hydrolysis Rates of Triarylmethyl Groups Attached to the 5'-Hydroxyl of Deoxnucleosides[1]

| Triarylmethyl Group[2] | Deoxy-nucleo-side[3] | $t_{\frac{1}{2}}$ (sec) in H+ | Color in Acid | Time (sec) to Complete Hydrolysis |
|---|---|---|---|---|
| $R_1 = n; R_2 = c; R_3 = a$ | T | 30 | Green | 45 |
| $R_1 = n; R_2 = e; R_3 = a$ | T | 180 | Red | >600 |
| $R_1 = R_2 = c; R_3 = a$ | T | 0 | Orange | 30 |
| $R_1 = R_2 = b; R_3 = n$ | T | 45 | Blue | 90 |
| $R_1 = R_2 = c; R_3 = a$ | C | 0 | Orange | 30 |
| $R_1 = R_2 = b; R_3 = n$ | C | 45 to 60 | Blue | 120 |
| $R_1 = R_2 = b; R_3 = a$ | G | 15 | Black | 45 |
| $R_1 = R_2 = c; R_3 = a$ | G | 0 | Orange | 30 |
| $R_1 = h; R_2 = R_3 = a$ | A | 60 | Yellow | 240 |
| $R_1 = R_2 = c; R_3 = a$ | A | 0 | Orange | 30 |

[1] Reaction conditions were 2% toluenesulfonic acid in chloroform:methanol (7:3). Aliquots were removed from the reaction solution, quenched with ammonium acetate and analyzed visually after tlc and exposure to HCl vapors. Time points were taken at 15, 30, 45, 60, 90, 120, 240, 300, and 600 sec.
[2] The aromatic functional groups are defined in the legend to Table 1.
[3] The symbols T, C, G and A refer to the nucleosides thymidine, N—benzoyldeoxycytidine, N—isobutyrldeoxyguanosine, and N—benzoyldeoxyadenosine. The nucleoside 5'-hydroxyl was derivatized to contain the triarylmethyl group.

TABLE IX

Table IX provides the spectral characteristics of selected triarylmethyl alcohols.

| Triarylcarbinol[1] | λ Maximum(s)[2] (nanometers) | Extinction Coefficient (Molar$^{-1}$ cm$^{-1}$) |
|---|---|---|
| $R_1 = R_2 = b; R_3 = a$ | 423 | 9300 |
| | 503 | 5200 |
| | 586 | 3900 |
| $R_1 = R_2 = a; R_3 = h$ | 452 | 42000 |

TABLE IX-continued

Table IX provides the spectral characteristics of selected triarylmethyl alcohols.

| Triarylcarbinol[1] | λ Maximum(s)[2] (nanometers) | Extinction Coefficient (Molar$^{-1}$ cm$^{-1}$) |
|---|---|---|
| $R_1$ = a; $R_2$ = c; $R_3$ = n | 545 | 25000 |
|  | 455 | 28000 |
| $R_1$ = $R_2$ = b; $R_3$ = N | 586 | 15500 |
| $R_1$ = a; $R_2$ = n; $R_3$ = c | 577 | 9500 |
|  | 421 | 20500 |

[1]See the legend to Table 1 for a definition of the functional groups $R_1$, $R_2$ and $R_3$.
[2]All spectra were taken in a saturated $ZnBr_2$ nitromethane solution. All spectra were recorded on a Carey model 21, scanning from 350 nm to 600 nm.

Four deoxyolignucleodides were synthesized using color coded deoxynucleotide phosphoramidites. The compounds were d(G-T-A-T-A-A-C-A-C), d(C-A-T-A-A-A-G-A-A-A-A-A), d(G-T-A-C-A-G-C-T-G-G-C-T) and d(C-C-C-T-T-T-C-T-T-A-A-A). The 5'-hydroxyl of each deoxynucleotide was protected with a different triarylmethyl group. These groups as assigned for the synthesis of deoxyoligonucleotides are listed in Table X.

TABLE X

| Triarylmethyl Group[1] | Deoxynucleoside | Color[2] |
|---|---|---|
| $R_1$ = $R_2$ = b; $R_3$ = n | N—benzoyldeoxycytidine | Blue |
| $R_1$ = h; $R_2$ = $R_3$ = a | N—benzoyldeoxyadenosine | Yellow |
| $R_1$ = c; $R_2$ = n; $R_3$ = a | Deoxythymidine | Red |
| $R_1$ = $R_2$ = c; $R_3$ = a | N—isobutyrldeoxyguanosine | Orange |

[1]The aromatic functional groups are defined in the legend to Table 1.
[2]The color of the triarylmethyl group is observed when the 5'-triarylphenyl deoxynucleoside is exposed to either protic or Lewis acids.

Thus the 5'-triarylmethyl groups of N-benzoyldeoxyadenosine, N-benzoyldeoxycytidine, N-isobutyrldeoxyguanosine and deoxythymidine produced yellow, blue, orange and red colors respectively when exposed to either Lewis or protic acids. These triarylmethyldeoxynucleosides were synthesized as outlined in this disclosure. Conversion to the appropriate 5'-O-triarylmethyl and deoxynucleoside N,N-dimethylaminomethoxyphosphines was completed using the procedure of Example VIII.

EXAMPLE VIII

General synthesis of 5'-triarylmethyl deoxynucleosides 5 mmoles of N-protected deoxynucleoside or thymidine is dissolved in 50 ml of dry pyridine. The sample is evaporated to a gum in vacuo. 25 ml of dry pyridine is added. Six mmoles of triarylmethyl chloride is added. The reaction mixture is shaken overnight. The reaction is monitored in methanol:chloroform (1:9). The product has an $R_f$ of 0.5 and the unreacted deoxynucleoside has an $R_f$ of 0.2. The reaction is quenched with 5 ml of absolute methanol.

After 30 minutes the reaction mixture is concentrated to a small volume, taken up in ethyl acetate and extracted once with water. The organic phase is dried over sodium sulfate and concentrated to a gum. 10 ml of toluene is added and then evaporated.

The reaction mixture is then taken up in chloroform and applied to a silica gel column (5 cm×20 cm) that has been equilibrated with 1% pyridine in chloroform. After the compound is loaded on the column, the column is washed with 500 ml of 1% pyridine in chloroform. The compound is eluted from the column with 3 to 6% methanol. The fractions containing the desired product are pooled, concentrated to a foam, taken up in chloroform and precipitated into hexane.

The precipitate is collected in a Büchner funnel and dried in vacuo. The average yield by weight is 85%.

The 5'-triarylmethyldeoxynucleosides were connected to the 3'-N,N-dimethylaminomethoxyphosphine compounds using the procedure of the preceeding examples. The synthesis of d(G-T-A-T-A-A-C-T-A-C-A-C) begins with N-benzoyldeoxycytidine attached covalently to silica gel through the 3'-hydroxyl. The next step was condensation with 5'-O-p-tolyldiphenylmethyl-N-benzoyl-deoxyadenosine 3'-N,N-dimethylaminomethoxyphosphine. After acylation and oxidation, detritylation was completed using a saturated solution of $ZnBr_2$ in nitromethane:methanol (19:1). A yellow color indicating the addition of N-benzoyldeoxyadenosine was observed. The remaining nucleotides were added in a similar manner. During each detritylation step, colors were observed in the following sequential order: blue, yellow, red, blue, yellow, red, yellow, red, and orange. These were the expected colors and confirm that the correct deoxyoligonucleotide was synthesized. Purification of the deoxyoligonucleotide was by reverse phase high performance liquid chromatography and polyacrylamide gel electrophoresis. Characterization was by two dimension sequence analysis (Sanger, Donelson, Coulson, Kossel, and Fischer, *Proc. Natl. Acad. Sci. USA* 70, 1209–1213, 1973). This analysis reconfirmed that the correct deoxyoligonucleotide had been synthesized as indicated by the colorimetric results. The three remaining deoxyoligonucleotides were synthesized and characterized in the same way.

For the synthesis of the four enumerated oligodioxynucleotides, the quantities of silica gel used and the choice of nucleoside joined to the silica gel support are summarized in Table XI.

TABLE XI

| Deoxyoligonucleotide | Nucleoside on Silica Gel | μmole Nucleoside/ Gram Silica Gel | Gram Silica Gel Used |
|---|---|---|---|
| d(G—T—A—T—A—A—C—T—A—C—A—C) | N—benzoyldeoxycytidine | 45 | 0.15 |
| d(C—A—T—A—A—A—G—A—A—A—A—A) | N—benzoyldeoxyadenosine | 40 | 0.15 |
| d(C—C—C—T—T—T—C—T—T—A—A—A) | N—benzoyldeoxyadenosine | 40 | 0.15 |
| d(G—T—A—C—A—G—C—T—G—G—C—T) | deoxythymidine | 53 | 0.15 |

Table XII summarizes physical parameters of 5'-O-triarylmethylnucleoside-3'-N,N-dimethylaminomethoxyphosphines used in the synthesis of the four enumerated oligodeoxynucleotides.

TABLE XII

| Nucleotide | M. Wt. | Phosphorus NMR Chemical Shifts (ppm)[1] | Color[2] |
|---|---|---|---|
| 5'-O—di-p-anisylphenylmethyl-N—isobutyryldeoxyguanosine-3'-N, | 746 | 146.3, 146.1 | Orange |

TABLE XII-continued

| Nucleotide | M. Wt. | Phosphorus NMR Chemical Shifts (ppm)[1] | Color[2] |
|---|---|---|---|
| N—dimethylaminomethoxyphosphine 5'-O—p-anisyl-1-naphthylphenyl-methyldeoxythymidine-3'-N,N—dimethylaminomethoxyphosphine | 659 | 146.4, 145.7 | Red |
| 5'-O—di-o-anisyl-1-napthylmethyl-N—benzoyldeoxycytidine-3'-N,N—dimethylaminomethoxyphosphine | 790 | 147.6, 145.4 | Blue |
| 5'-O—p-tolyldiphenylmethyl-N—benzoyl-deoxyadenosine-3'-N,N—dimethylamino-methoxyphosphine | 718 | 146.4, 146.1 | Yellow |

[1] Spectra were recorded in $CH_3CN$ as solvent and against phosphoric acid as external standard.
[2] Color produced in either a Lewis acid or a protic acid.

For each condensation step, 120 μmoles of the 5'-O-triarylmethylnucleotide, acetonitrile, and 480 μmole tetrazole were used. The next steps were acylation with acetic anhydride, oxidation with $I_2$ and detritylation with $ZnBr_2$. After each detritylation step, the expected color corresponding to the required trityl cation was observed.

Once each synthesis was complete, the deoxyoligonucleotide was isolated by the following procedure. Each deoxyoligonucleotide covalently bound to silica gel (30 mg) was first treated with thiophenol:triethylamine:dioxane (1:1:2) for 90 minutes, washed four times with methanol and then washed once with diethylether. The silica gel was isolated by centrifugation and air dried. Each sample was next treated with t-butylamine:methanol (1:1) for 18 hours at 50° C. The supernatants obtained after centrifugation were removed and dried in vacuo. The silica gel samples were next treated with concentrated ammonium hydroxide at room temperature for three hours in order to remove the deoxyoligonucleotide from the silica gel. The supernatants were transferred to test tubes containing the residues from the t-butylamine procedure and the solutions concentrated in vacuo. Fresh concentrated ammonium hydroxide was added to the dry residues and the solutions were warmed at 50° C. for 22 hours in order to remove amino protecting groups from deoxyoligonucleotide bases. The samples were concentrated in vacuo and each sample was next dissolved in 200 μl water. Purification was by reverse phase high performance liquid chromatography. The retention times and solvent conditions are outlined in Table XIII. Each deoxyoligonucleotide was next treated with 80% acetic acid at room temperature for 1 hour in order to remove the triarylphenylmethyl group. After concentration in vacuo, each sample was purified by polyacrylamide gel electrophoresis and analyzed as to the correct deoxymononucleotide sequence by two dimension sequence analysis.

TABLE XIII

| Deoxyoligonucleotide | % Acetonitrile[1] | Retention Time[2] |
|---|---|---|
| d(G—T—A—T—A—A—C—T—A—C—A—C)[3] | 29 | 2.6 |
|  | 27 | 3.8 |
|  | 26 | 6.2 |
| d(C—A—T—A—A—A—G—A—A—A—A—A)[4] | 30 | 2.9 |
|  | 28 | 3.0 |
|  | 26 | 4.5 |
| d(C—C—C—T—T—T—C—T—T—A—A—A)[4] | 30 | 2.9 |
|  | 26 | 4.6 |
|  | 25 | 7.2 |
|  | 24 | 9.8 |
| d(G—T—A—C—A—G—C—T—G—G—C—T)[5] | 29 | 2.6 |
|  | 27 | 3.6 |
|  | 25 | 6.3 |

[1] The aqueous buffer contains 0.1 M triethylammonium acetate.
[2] 1.2 min/k' 2.0 ml/min.
[3] Triarylmethyl group was di-p-anisylphenylmethyl, preparative isolation was at 25% acetonitrile.
[4] Triarylmethyl group was di-o-anisyl-1-napthylmethyl, preparative isolation was at 25% acetonitrile.
[5] Triarylmethyl group was di-p-anisylphenylmethyl, preparative isolation was at 24% acetonitrile.

What is claimed is:

1. A compound of the formula:

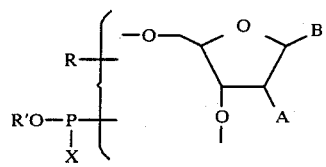

wherein B is a nucleoside or deoxynucleoside base; R is H or a blocking group, A is H or OR; R' is a hydrocarbyl radical containing up to 10 carbon atoms and X is a amino group formed by removal of the hydrogen atom from a ring nitrogen of a nitrogen heterocyclic compound which contains unsaturation in the ring structure.

2. A compound of the formula:

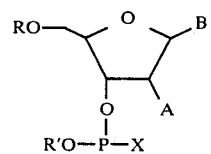

wherein B is a nucleoside or deoxynucleoside base; R is H or a blocking group; A is H or OR: R' is lower alkyl and X is a amino group formed by removal of the H atom of the amino nitrogen of a nitrogen heterocyclic compound.

3. The compound according to claim 1 or 2 wherein the amino group is tetrazolyl, nitroimidazolyl or triazolyl.

4. The compound according to claim 1 or 2 wherein B is thymine, cytosine, adenosine, uracil and guanine.

5. The compound according to claim 1 or 2 wherein R is a trityl group.

6. The compound according to claim 1 or 2 wherein R is di-p-anisylphenylmethyl or p-anisylphenylmethyl.

7. The compound according to claim 2 wherein A is H.

8. The compound according to claim 1 or 2 wherein R is di-p-anisylphenylmethyl, B is 9-(N-6-benzoyladeninyl), R' is methyl, A is H and X is tetrazolyl.

9. The compound according to claim 1 or 2 wherein R is di-p-anisylphenylmethyl, B is thyminyl, R' is methyl, A is H and X is tetrazolyl.

10. The compound according to claim 1 or 2 wherein R is di-p-anisylphenylmethyl, B is 1-cytosinyl, R' is methyl, A is H and X is tetrazolyl.

11. The compound according to claim 1 or 2 wherein R is di-p-anisylphenylmethyl, B is 9-(N-6-benzoyladeninyl), R' is methyl, A is H and X is tetrazolyl.

12. The compound according to claim 1 or 2 wherein R is di-p-anisylphenylmethyl, B is 9-guaninyl, R' is methyl, A is H and X is tetrazolyl.

13. The compound according to claim 10 wherein B is 1-(N-4-acetylcytosine), 1-(N-benzoylcytosine, or 1-(N-isobutyrylcytosine).

14. The compound according to claim 12 wherein B is 9-(N-6-benzoylguaninyl), 9-(N-6-acetylguaninyl), or 9-(N-6-isobutyrylguaninyl).

15. The compound according to claim 8 wherein B is 9-(N-6-acetyladeninyl) or 9-(N-6-isobutyryladeninyl).

16. The compound according to claim 11 wherein B is 9-(N-6-acetyladeninyl) or 9-(N-6-isobutyryladeninyl).

* * * * *

UNITED STATES PATENT AND TRADEMARK OFFICE
CERTIFICATE OF CORRECTION

PATENT NO. : 4,500,707
DATED : February 19, 1985
INVENTOR(S) : Marvin H. Caruthers and Mark D. Matteucci It is certified that error appears in the above—identified patent and that said Letters Patent is hereby corrected as shown below:

Column 5, line 54 delete "P" and insert --$\circled{P}$--.

Column 6, lines 38, 52, and 67, delete "P" (each occurrence) and insert --$\circled{P}$-- (each occurrence).

Column 25, line 7 delete "$R_8$" and insert --$R_3$--.

Column 26, line 44 delete "$R_1=R_2=g; R_3=a$" and insert --$R_1=c; R_2=g; R_3=a$--.

Signed and Sealed this

Twentieth Day of May 1986

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,500,707
DATED : February 19, 1985
INVENTOR(S) : Marvin H. Caruthers and Mark D. Matteucci It is certified that error appears in the above-identified patent and that said Letters Patent is hereby corrected as shown below:

Column 23, line 37 delete "isobutynldeoxyguanosine" and insert --isobutyryldeoxyguanosine--.

Signed and Sealed this

Eighteenth Day of November, 1986

*Attest:*

DONALD J. QUIGG

*Attesting Officer*   *Commissioner of Patents and Trademarks*